US012702309B2

(12) United States Patent
Derkx

(10) Patent No.: US 12,702,309 B2
(45) Date of Patent: Aug. 11, 2026

(54) METHOD, APPARATUS AND COMPUTER PROGRAM PRODUCT FOR ANALYSING A PULSE WAVE SIGNAL TO DETERMINE AN INDICATION OF BLOOD PRESSURE AND/OR BLOOD PRESSURE CHANGE

(71) Applicant: KONINKLIJKE PHILIPS N.V., Eindhoven (NL)

(72) Inventor: Rene Martinus Maria Derkx, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 208 days.

(21) Appl. No.: 18/276,277

(22) PCT Filed: Feb. 28, 2022

(86) PCT No.: PCT/EP2022/054923

§ 371 (c)(1),
(2) Date: Aug. 8, 2023

(87) PCT Pub. No.: WO2022/184610

PCT Pub. Date: Sep. 9, 2022

(65) Prior Publication Data

US 2024/0115145 A1 Apr. 11, 2024

(30) Foreign Application Priority Data

Mar. 3, 2021 (EP) .................................... 21160541

(51) Int. Cl.
*A61B 5/021* (2006.01)
*A61B 5/00* (2006.01)

(52) U.S. Cl.
CPC ........ *A61B 5/02108* (2013.01); *A61B 5/7242* (2013.01); *A61B 5/7246* (2013.01); *A61B 2560/0223* (2013.01)

(58) Field of Classification Search
CPC ....... A61B 5/022; A61B 5/0004; A61B 5/742; A61B 5/02108; A61B 2562/08; A61B 5/02141; A61B 5/02233
See application file for complete search history.

(56) References Cited

U.S. PATENT DOCUMENTS 5,533,511 A 7/1996 Kaspari
6,485,431 B1 11/2002 Campbell
(Continued)

FOREIGN PATENT DOCUMENTS

CN 104983412 A 10/2015
CN 111870237 A 11/2020
(Continued)

OTHER PUBLICATIONS

International Search Report Dated Jun. 10, 2022 for International Appln No. PC/EP2022/054923 Filed Feb. 28, 2022.
(Continued)

*Primary Examiner* — Justin Xu
(74) *Attorney, Agent, or Firm* — Brynne J. Corcoran

(57) ABSTRACT

According to an aspect, there is provided a computer-implemented method for analysing a pulse wave signal, PWS, obtained from a subject to determine an indication of the blood pressure or a change in blood pressure of the subject. The PWS comprises pulse wave measurements for a plurality of cardiac cycles of the subject during a first time period. The method comprises (i) analysing (111) the PWS to determine a first average cardiac cycle waveform for a first time point in the first time period and a second average cardiac cycle waveform for a second time point in the first time period; (ii) determining (113) a difference signal representing a change in morphology from the first average cardiac cycle waveform to the second average cardiac cycle waveform; (iii) determining (115) an absolute value of the change in morphology from the difference signal; (iv) deter- (Continued)

Analyse the PWS to determine a first average cardiac cycle waveform for a first time point in the first time period and a second average cardiac cycle waveform for a second time point in the first time period — 111

Determine a difference signal representing a change in morphology from the first average cardiac cycle waveform to the second average cardiac cycle waveform — 113

Determine an absolute value of the change in morphology from the difference signal — 115

Determine a direction of the change in morphology — 117

Determine a relative blood pressure change by combining the absolute value and the direction of the change in morphology — 119 mining (117) a direction of the change in morphology; and (v) determining (119) a relative blood pressure change by combining the absolute value and the direction of the change in morphology.

15 Claims, 14 Drawing Sheets

(56) References Cited

U.S. PATENT DOCUMENTS

| | | | |
|---|---|---|---|
| 8,273,030 | B2 | 9/2012 | Harpas |
| 11,647,910 | B2 | 5/2023 | McCombie |
| 2009/0326386 | A1 | 12/2009 | Sethi |
| 2010/0081946 | A1 | 4/2010 | Garudadri |
| 2012/0078123 | A1 | 3/2012 | Futatsuyama |
| 2018/0199893 | A1 | 7/2018 | Hubmer |

FOREIGN PATENT DOCUMENTS

| | | | |
|---|---|---|---|
| EP | 4014837 | A1 | 6/2022 |
| JP | 2010075232 | A | 4/2010 |
| JP | 2020146140 | A | 9/2020 |
| WO | 2015044010 | A1 | 4/2015 |
| WO | 2022128830 | A1 | 6/2022 |

OTHER PUBLICATIONS

D.J. Korteweg, "Uber die fortpflanzungs-geschwindigkeit des schalles in elastischen rohren", Annalen der Physik und Chemie, vol. 5, pp. 525-542, 1878.

E.R. Nye, "The effect of blood pressure alteration on the pulse wave velocity", Brit. Heart. J. 1964, vol. 26, pp. 261-265.

D.J. Hughes and C.F. Babbs and L.A. Geddes and J.D. Bourland, "Measurements of Young's Modulus of Elasticity of the Canine Aorta with Ultrasound" (1979), WIdon School of Biomedical Engineering Faculty Publications. Paper 52.

Xiaoman Xing & Mingshan Sun, "Optical Blood Pressure Estimation With Photoplethysmography and FFT-Based Neural Networks", Biomedical Optics Express 3007-3020, vol. 7 No. 8.

G.P. Ramdas and P.M. Shah, "Relationship between the pulse wave and flow velocity wave and their propagation velocities in the arterial system: Implications for the assessment of regional physical properties of the arterial beds", International Journal of Angiology 1999, vol. 8, pp. 127-130.

S.I. Rabben and N. Stergiopulos and L.R. Hellevik and O. A. Smiseth and S. Slordahl and S. Urheim and B. Angelsen, "An ultrasound-based method for determining pulse wave velocity in superficial arteries", J. Biomech. 2004, vol. 37 (10), pp. 1615-1622.

S.C. Millasseau and R.P. Kelly and J.M. Ritterand P.J. Chowienczyk, "Determination of age-related increases in large artery stiffness by digital pulse contour analysis", Clinical Science (2002), vol. 103, pp. 371-377.

F.C. Bennis and C. van Pul and J.J.L. van den Bogaart and P. Andriessen and B.W. Kramer and T. Delhaas, "Artifacts in pulse transit time measurements using standard patient monitoring equipment", PLOS One, Jun. 2019, pp. 1.10.

Wen-Rong Yan, Rong-Chao Peng, Yuan-Ting Zhang & Derek Ho, "Cuffless Continuous Blood Pressure Estimation From Pulse Morpholoty of Photoplethysmograms", IEEE Access, Aug. 24, 2019, vol. 7, 2019,pp. 141970-141977.

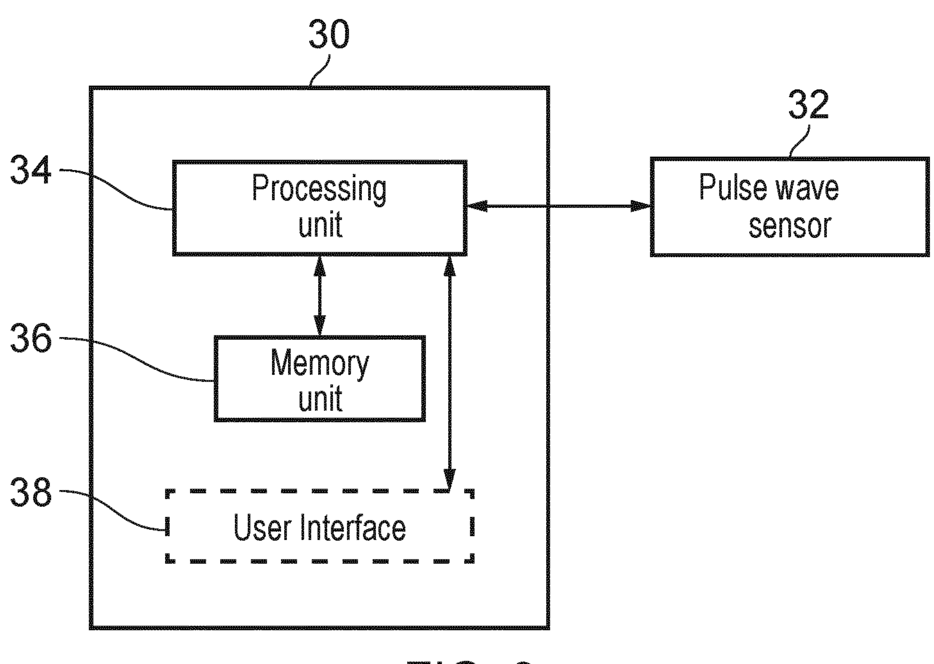

FIG. 3

Analyse PWS to identify a plurality of cardiac cycles and a reference point for each cycle — 40

↓

For a first lag time value, determine an n-th order polynomial fit for a first set of values of a second derivative with respect to time of the PWS — 42

↓

Perform one or more further iterations of step 42 for one or more further lag time values — 44

↓

Form a first average cardiac cycle waveform for a first time point in the first time period — 46

FIG. 4

METHOD, APPARATUS AND COMPUTER PROGRAM PRODUCT FOR ANALYSING A PULSE WAVE SIGNAL TO DETERMINE AN INDICATION OF BLOOD PRESSURE AND/OR BLOOD PRESSURE CHANGE

CROSS-REFERENCE TO PRIOR APPLICATIONS

This application is the U.S. National Phase application under 35 U.S.C. § 371 of International Application No. PCT/EP2022/054923, filed on Feb. 28, 2022, which claims the benefit of European Application No. 21160541.5 filed on Mar. 3, 2021. These applications are hereby incorporated by reference herein.

FIELD OF THE INVENTION

This disclosure relates to pulse wave signals obtained from a subject, with the pulse wave signal comprising pulse wave measurements for a plurality of cardiac cycles of the subject. More particularly, this disclosure relates to a method, apparatus and a computer program product for analysing pulse wave signals to determine an indication of blood pressure and/or blood pressure change of the subject.

BACKGROUND OF THE INVENTION

Blood pressure (BP) is an important indicator of health in a person/subject. In the US it is estimated about 30% of the adult population has high blood pressure. Hypertension is a common health problem which has no obvious outward symptoms. Blood pressure generally rises with aging and the risk of becoming hypertensive in later life is considerable. Persistent hypertension is one of the key risk factors for strokes, heart failure and increased mortality. The condition of a subject can be improved by lifestyle changes, healthy dietary choices and medication. Particularly for high risk patients, continuous 24-hour blood pressure monitoring is very important by means of systems which do not impede ordinary daily life activities. Continuous monitoring of blood pressure can also be useful for patients in a healthcare environment, such as a hospital e.g. in the operating room (OR) or the Intensive Care Unit (ICU). A low blood pressure can lead to a poor oxygenation of important organs and could result in organ damage. A too high blood pressure can cause bleeding which should be prevented especially during and after surgical procedures, specifically in brain surgeries.

In some cases absolute measurements of blood pressure can be obtained, and in other cases relative measurements of blood pressure can be obtained, for example a measurement of a change in blood pressure. In particular, blood pressure can change over short time windows, e.g. of the order of a few minutes, and these changes can be relevant for further medical examination and possibly medical intervention.

There are a number of different techniques available for measuring blood pressure, and/or changes in blood pressure. Some of these techniques measure blood pressure itself, while other techniques measure other physiological characteristics of the subject and use these as surrogates for blood pressure, for example by relating changes or values of the physiological characteristic to changes or values of blood pressure. Some of the techniques for directly measuring blood pressure require invasive access to the arteries of the subject, or the use of bulky/inconvenient equipment such as inflatable cuffs. However, some of the physiological characteristics used as surrogates for blood pressure can be measured using simple and/or unobtrusive sensors applied to the body of the subject.

Tonometry uses an externally placed force or pressure sensor to measure arterial distension (i.e. a waveform representing the distension of the artery) as pressure is applied to the artery. Alternatively one or more photoplethysmography (PPG) sensors can be placed on a part of the body to obtain one or more PPG signals that represent the changes in volume of the blood flow in the body part during a number of heart cycles (cardiac cycles). Both of these techniques obtain a pulse wave signal (PWS) from the subject that covers a number of cardiac cycles of the subject. This pulse waveform/signal can be analysed to determine one or more physiological characteristics that are used as surrogate blood pressure measurements.

One physiological characteristic that can be used as a surrogate blood pressure measurement is pulse wave velocity (PWV). When the heart beats, a pulse wave is generated through the blood of the aorta and the further arterial system. The speed of the pulse wave (called pulse wave velocity) is influenced by blood (fluid) properties and some arterial properties (like diameter and compliance). These blood properties and arterial properties are also influenced by blood pressure, and so changes in PWV can be linked to changes in blood pressure.

Some techniques for measuring PWV use a two-spot or dual-spot approach. This requires two sensors (e.g. PPG sensors) in order to capture two signals simultaneously. The signal from the first sensor is used to detect the onset of the pulse wave at a proximal location, e.g. close to the heart. The signal from the second signal is used to detect the arrival of the pulse wave at a distal location, e.g. at the femoral artery of the finger of the patient.

However, to minimise the inconvenience for the subject due to the measurement equipment, single-spot techniques for measuring PWV are being developed. These techniques make use of pulse wave reflections in the arterial tree. There is a direct pulse wave traveling from the aorta to, for example, the finger, and there is an indirect pulse wave that first travels from the aorta to the renal bifurcation and then travels from the renal bifurcation to the finger. In this way, the indirect (reflected) pulse wave arrives later at the finger location than the direct pulse wave. When the arrival times of the direct and indirect pulse waves are measured at the finger, a subtraction of these arrival times gives the time required to travel from the aortic arch to the renal bifurcation and back. With knowledge (or an approximation) of this extra travel distance of the reflected pulse wave, it is possible to estimate the pulse wave velocity of the reflected wave according to Equation (1) below:

$$PWV_s = \frac{2 \cdot L_{hr}}{t_c - t_a} \triangleq \frac{2 \cdot L_{hr}}{PRT}, \tag{1}$$

where $L_{hr}$ is the distance between the aortic arch and the renal bifurcation and PRT is the so-called pulse reflection time, which is defined as the time between the start (up-flank) of the direct pulse wave until the time of the start (up-flank) of the indirect pulse wave. The times $t_c$ and $t_a$ required to compute the PRT can be determined via the so-called "acceleration waveform" of the PPG measurement, that is obtained via, e.g. double-differentiation of the PPG waveform with respect to time.

Typically, it is assumed that the acceleration waveform consists of five 'fiducial points' or 'reference points', as shown in FIG. 1. FIG. 1(*a*) shows an exemplary PPG signal covering a 1 second period with the dicrotic notch indicated. FIG. 1(*b*) shows a first derivative of the PPG signal of FIG. 1(*a*) with respect to time, and FIG. 1(*c*) shows a second derivative of the PPG signal of FIG. 1(*a*) with respect to time. The first derivative is denoted v-PPG and the second derivative (acceleration waveform) is denoted a-PPG. The five reference points are shown in the acceleration waveform, FIG. 1(*c*). The a point marks the start of the direct pulse wave and the b point marks the end of the direct pulse wave. The e point marks the end of the systolic period (aortic valve closure), and for the purposes of this disclosure it is assumed that the c point marks the start of the reflected wave and the d point marks the end of the reflected wave.

FIG. 2 shows an example of a single-spot PPG measurement and PWV derivation according to Equation (1). The graph in FIG. 2(*a*) shows the mean arterial pressure (MAP) in mmHg over a period of 5 hours of an ICU patient. The graph in FIG. 2(*b*) shows PWV in m/s calculated from a PPG signal according to Equation (1), with an estimation of 2 $L_{hr}$ (twice the heart to the renal bifurcation distance) as 75 cm.

It can be seen in FIG. 2 that there is a strong positive correlation between the MAP and the pulse wave velocity from the single-spot measurement. However, the robustness of the pulse wave velocity measurement can be questioned since there are a lot of outliers in the pulse wave velocity values, particularly when compared to pulse wave velocity derived from a two-spot measurement approach.

SUMMARY OF THE INVENTION

Part of the problem with the single-spot pulse wave velocity measurement is that the fiducial points of the reflected pulse waves are not always easy to detect. This can be seen from the a-PPG plot in FIG. 1(*c*). Computing a second derivative of this PPG signal leads to a very poor signal because of the quantization and noise in the original PPG signal. Signal smoothing (either temporal or over multiple cardiac cycles) can be applied in order to obtain improved fiducial point detections. After such smoothing, it becomes possible to robustly detect the fiducial points. However, for a good detection of the c and d points (which relate to the reflected wave) quite substantial smoothing needs to be applied before the fiducial points can be robustly detected. Too much temporal smoothing leads to loss in the high-frequency fiducial points, whereas too much averaging over multiple cardiac cycles gives problems under time varying conditions).

One way to obtain a surrogate blood pressure measurement based on PWV is to detect the c point or c-waves in the averaged cardiac cycle waveforms and to measure the time between the a point and the c point, in a similar way to the PRT-based approach described above. However, the c point does not always show-up as a clear local maximum; this is often the case for elderly persons with stiff arteries. Therefore, to improve the robustness and reliability of surrogate blood pressure measurements, it may be beneficial to avoid having to detect fiducial points in the averaged cardiac cycle waveform. Therefore there is a need for improvements in determining an indication of the blood pressure or a change in blood pressure of a subject from averaged cardiac cycle waveforms.

The techniques described herein avoid the use of late systole period fiducial point detection in the computation of a surrogate blood pressure measurement by defining an alternative way to compute a surrogate blood pressure measurement from a morphology change of the average cardiac cycle waveform.

According to a first specific aspect, there is provided a computer-implemented method for analysing a pulse wave signal, PWS, obtained from a subject to determine an indication of the blood pressure or a change in blood pressure of the subject. The PWS comprises pulse wave measurements for a plurality of cardiac cycles of the subject during a first time period. The method comprises (i) analysing the PWS to determine a first average cardiac cycle waveform for a first time point in the first time period and a second average cardiac cycle waveform for a second time point in the first time period; (ii) determining a difference signal representing a change in morphology from the first average cardiac cycle waveform to the second average cardiac cycle waveform; (iii) determining an absolute value of the change in morphology from the difference signal; (iv) determining a direction of the change in morphology; and (v) determining a relative blood pressure change by combining the absolute value and the direction of the change in morphology. Thus the method provides that an indication of the blood pressure or a change in blood pressure of a subject can be determined from averaged cardiac cycle waveforms without having to detect fiducial points in the late systole period of the cardiac cycle where typically the detections of fiducial points are very difficult and hence erroneous.

In some embodiments, step (iv) comprises determining the direction of the change in morphology from the difference signal. These embodiments have the benefit that a separate sensor or measurement signal is not required to determine the direction of the change in morphology.

In alternative embodiments, step (iv) comprises: analysing a pulse arrival time, PAT, signal for the subject during the first time period to determine a relative PAT change from the first time point to the second time point; and determining the direction of the change in morphology as the direction of the relative PAT change.

In some embodiments, step (v) comprises multiplying the absolute value and the direction of the change in morphology to determine the relative blood pressure change.

In some embodiments, step (i) comprises analysing the PWS to identify a plurality of cardiac cycles and a respective reference point for each identified cardiac cycle.

In some embodiments, the method further comprises (vi) integrating the relative blood pressure change with respect to time to determine an estimate of blood pressure of the subject.

In some embodiments, step (vi) comprises determining the estimate of blood pressure using the absolute value, the direction of the change in morphology, and a first measure of quality of the relative blood pressure change.

In these embodiments, step (vi) further comprises determining the first measure of quality of the relative blood pressure change by computing a goodness of fit of the first and second average cardiac waveform to the plurality of cardiac cycles in the PWS.

In some embodiments, the difference signal comprises respective difference samples for a plurality of lag time values measured with respect to a respective reference point for the first average cardiac cycle waveform and the second average cardiac cycle waveform, wherein a difference sample for a particular lag time value is the difference between the first average cardiac cycle waveform at the particular lag time value and the second average cardiac cycle waveform at the particular lag time value.

In these embodiments, the reference point can be an onset of a pulse wave of the subject, and the plurality of lag time values can be lag time values from 0 milliseconds to 300 milliseconds after the reference point. In these embodiments, step (iii) can comprise determining the absolute value of the change in morphology as the sum of the magnitude of the difference samples for the plurality of lag time values. In these embodiments, step (iv) can comprise determining the sum of the difference samples for a subset of the plurality of lag time values; and determining the direction of the change in morphology as the sign of the sum of the difference samples. In these embodiments, the reference point can be an onset of a pulse wave of the subject, and the subset of the plurality of lag time values can be lag time values after the reference point. In these embodiments, the subset of the plurality of lag time values can be lag time values from 75 milliseconds to 150 milliseconds after the reference point. These lag time values are those parts of the PWS that are influenced by reflection waves. In these embodiments, each of the time lag values can be equal to or less than a duration of a cardiac cycle of the subject.

In some embodiments, the PWS is a photoplethysmogram, PPG, signal.

According to a second specific aspect, there is provided an apparatus for analysing a pulse wave signal, PWS, obtained from a subject to determine an indication of the blood pressure or a change in blood pressure of the subject. The PWS comprises pulse wave measurements for a plurality of cardiac cycles of the subject during a first time period. The apparatus is configured to: (i) analyse the PWS to determine a first average cardiac cycle waveform for a first time point in the first time period and a second average cardiac cycle waveform for a second time point in the first time period; (ii) determine a difference signal representing a change in morphology from the first average cardiac cycle waveform to the second average cardiac cycle waveform; (iii) determine an absolute value of the change in morphology from the difference signal; (iv) determine a direction of the change in morphology; and (v) determine a relative blood pressure change by combining the absolute value and the direction of the change in morphology. Thus the apparatus enables an indication of the blood pressure or a change in blood pressure of a subject to be determined from averaged cardiac cycle waveforms without having to detect fiducial points in the late systole period of the cardiac cycle where typically the detections of fiducial points are very difficult and hence erroneous.

Various embodiments of the apparatus are contemplated in which the processing unit is further configured to operate according to any of the embodiments of the first aspect set out above.

In some embodiments, the apparatus further comprises a pulse wave sensor for obtaining the PWS from the subject. In alternative embodiments, the apparatus is configured to receive the PWS from a pulse wave sensor.

According to a third aspect, there is provided a computer program product comprising a computer readable medium having computer readable code embodied therein, the computer readable code being configured such that, on execution by a suitable computer or processing unit, the computer or processing unit is caused to perform the method according to the first aspect or any embodiment thereof. These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which:

FIG. 3 is a block diagram of an apparatus according to various exemplary embodiments;

FIG. 4 is a flow chart illustrating a method for analysing a pulse wave signal obtained from a subject to determine an average cardiac cycle waveform;

DETAILED DESCRIPTION OF EMBODIMENTS

Figure 1:
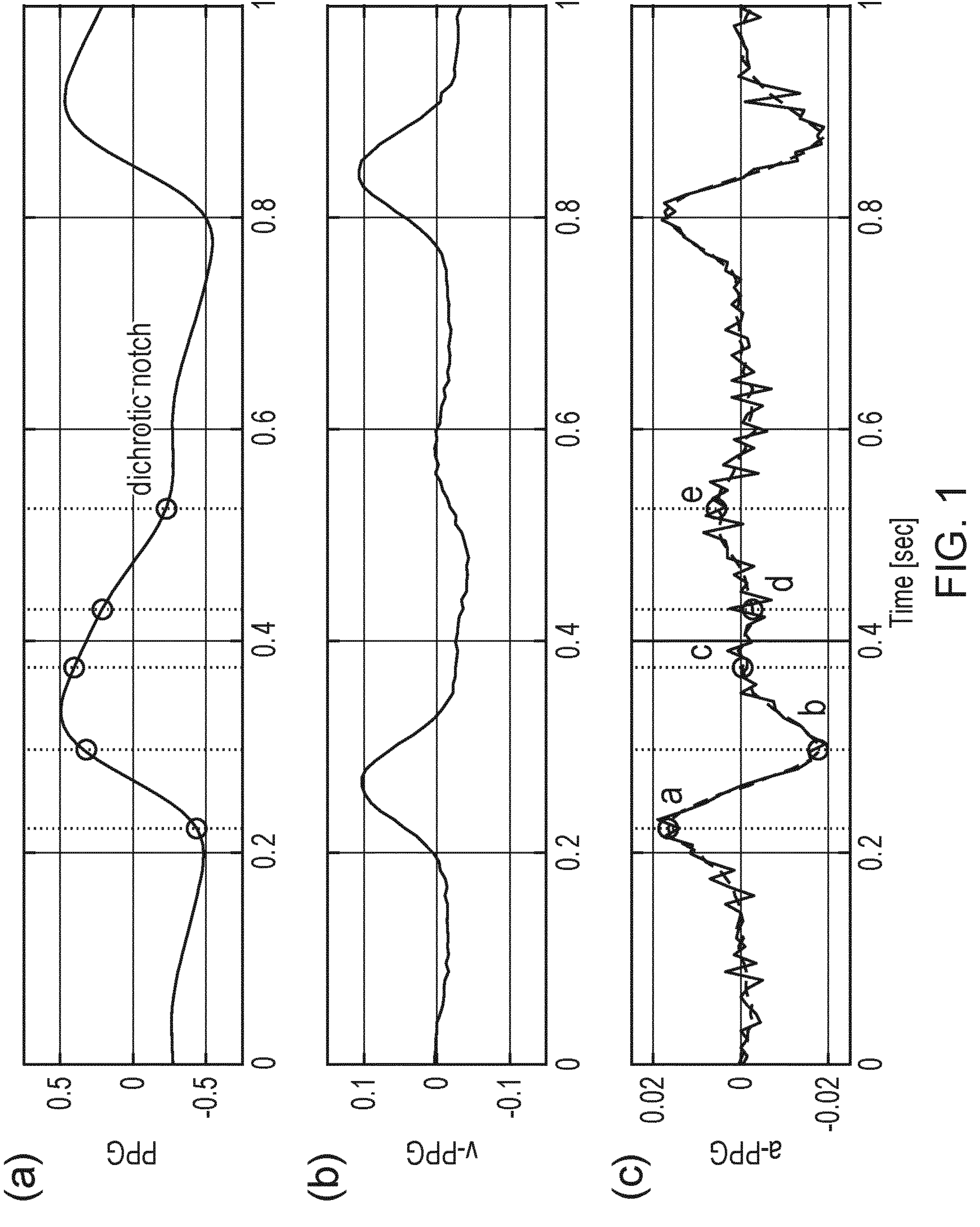
FIG. 1(*a*) shows a 1-second segment of a PPG signal, and FIGS. 1(*b*) and 1(*c*) show the first and second derivatives of the PPG signal respectively.
Figure 2:
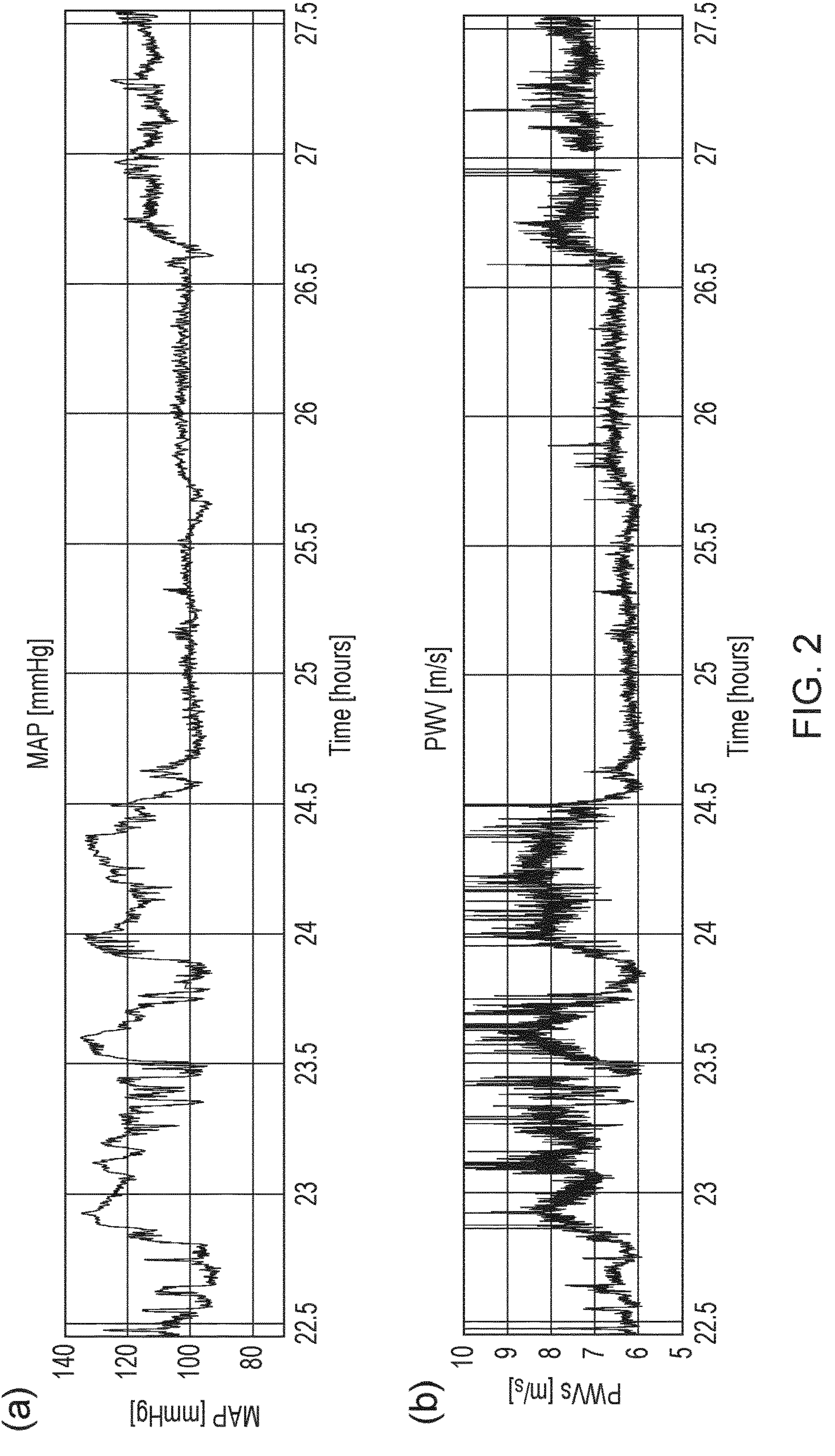
FIG. 2(*a*) shows a measurement of mean arterial pressure over a 5-hour time period, and FIG. 2(*b*) shows an example of a single-spot PPG measurement and PWV derivation according to Equation (1) for the same time period.

The techniques described herein avoid the use of fiducial point detection in the computation of a surrogate blood pressure measurement by defining an alternative way to compute a surrogate blood pressure measurement from a morphology change of the average cardiac cycle waveform. In particular, a relative blood pressure change can be determined from an absolute value of a change in morphology across two average cardiac cycle waveforms and a direction of the morphology change. The described techniques are particularly useful for the so-called single-spot measurement techniques where a single sensor is applied to a subject.

A pulse wave signal (PWS) includes information about pulse changes/pulse waves at a measurement point on a body of a subject. The PWS can be, e.g., a PPG signal, or a pulse wave signal obtained using tonometry.

FIG. 3 is a block diagram of an apparatus 30 for analysing a PWS according to various embodiments of the techniques described herein to determine a relative blood pressure change. A pulse wave sensor 32 is shown in FIG. 3 that is used to measure pressure waves at a single point on the body of a subject and to output a PWS. The pulse wave sensor 32 can be a PPG sensor, a tonometry-based sensor or a hydraulic sensor pad that can be applied with some application pressure to the (upper) arm of the subject and using a pressure sensor of any type, e.g. the MPXV6115 Series Integrated Silicon Pressure Sensor from NXP Semiconductors. In some embodiments, the pulse wave sensor 32 can be part of, or integral with, the apparatus 30. In other embodiments, the apparatus 30 can be connected to the pulse wave sensor 32, either directly (e.g. wired) or indirectly (e.g. using a wireless communication technology such as Bluetooth, WiFi, a cellular communication protocol, etc.). In alternative embodiments, the apparatus 30 may not be connected to the pulse wave sensor 32, and instead the apparatus 30 can obtain the PWS from another device or apparatus, such as a server or database.

As is known, a PPG sensor 32 can be placed on the body of the subject, for example on an arm, leg, earlobe, finger, etc., can provide an output signal (a 'PPG signal') that is related to the volume of blood passing through that part of the body. The volume of blood passing through that part of the body is related to the pressure of the blood in that part of the body. A PPG sensor 32 typically comprises a light sensor, and one or more light sources. The PPG signal output by the PPG sensor 32 may be a raw measurement signal from the light sensor (e.g. the PPG signal can be a signal representing light intensity over time). Alternatively, the PPG sensor 32 may perform some pre-processing of the light intensity signal, for example to reduce noise and/or compensate for motion artefacts, but it will be appreciated that this pre-processing is not required for the implementation of the techniques described herein.

The apparatus 30 may be in the form of, or be part of, a computing device, such as a server, desktop computer, laptop, tablet computer, smartphone, smartwatch, etc., or a type of device typically found in a clinical environment, such as a patient monitoring device (e.g. a monitoring device located at the bedside of a patient in a clinical environment) that is used to monitor (and optionally display) various physiological characteristics of a subject/patient.

The apparatus 30 includes a processing unit 34 that controls the operation of the apparatus 30 and that can be configured to execute or perform the methods described herein to analyse the PWS. The processing unit 34 can be implemented in numerous ways, with software and/or hardware, to perform the various functions described herein. The processing unit 34 may comprise one or more microprocessors or digital signal processors (DSPs) that may be programmed using software or computer program code to perform the required functions and/or to control components of the processing unit 34 to effect the required functions. The processing unit 34 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), field-programmable gate arrays (FPGAs), hardware for implementing a neural network and/or so-called artificial intelligence (AI) hardware accelerators (i.e. a processor(s) or other hardware specifically designed for AI applications that can be used alongside a main processor).

The processing unit 34 is connected to a memory unit 36 that can store data, information and/or signals for use by the processing unit 34 in controlling the operation of the apparatus 30 and/or in executing or performing the methods described herein. In some implementations the memory unit 36 stores computer-readable code that can be executed by the processing unit 34 so that the processing unit 34 performs one or more functions, including the methods described herein. In particular embodiments, the program code can be in the form of an application for a smartwatch, smartphone, tablet, laptop or computer. The memory unit 36 can comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM) and electrically erasable PROM (EEPROM), and the memory unit 36 can be implemented in the form of a memory chip, an optical disk (such as a compact disc (CD), a digital versatile disc (DVD) or a Blu-Ray disc), a hard disk, a tape storage solution, or a solid state device, including a memory stick, a solid state drive (SSD), a memory card, etc.

In some embodiments, the apparatus 30 comprises a user interface 38 that includes one or more components that enables a user of apparatus 30 to input information, data and/or commands into the apparatus 30, and/or enables the apparatus 30 to output information or data to the user of the apparatus 30. Information that can be output by the user interface 38 can include an indication of a determined relative blood pressure change, and in some embodiments an indication of an absolute blood pressure for the subject. The user interface 38 can comprise any suitable input component(s), including but not limited to a keyboard, keypad, one or more buttons, switches or dials, a mouse, a track pad, a touchscreen, a stylus, a camera, a microphone, etc., and/or the user interface 38 can comprise any suitable output component(s), including but not limited to a display screen, one or more lights or light elements, one or more loudspeakers, a vibrating element, etc.

Although not shown in FIG. 3, the apparatus 30 may comprise one or more additional sensors for measuring physiological characteristics of a subject, or the processing unit 34 can be configured to receive measurement signals from one or more additional sensors. In some embodiments, an additional sensor in the form of an electrocardiogram (ECG) sensor is provided to measure the electrical activity of the heart.

It will be appreciated that a practical implementation of an apparatus 30 may include additional components to those shown in FIG. 3. For example the apparatus 30 may also include a power supply, such as a battery, or components for enabling the apparatus 30 to be connected to a mains power supply. The apparatus 30 may also include interface circuitry for enabling a data connection to and/or data exchange with other devices, including the pulse wave sensor 32 (in embodiments where the pulse wave sensor 32 is separate from the apparatus 30), servers, databases, user devices and/or other sensors.

As noted above, the techniques described herein provide that a relative blood pressure change can be determined from an absolute value of a change in morphology across two average cardiac cycle waveforms and a direction of the morphology change. The two average cardiac cycle waveforms can be determined from a second derivative of a PWS that comprises pulse wave measurements for a number of cardiac cycles of the subject in a particular time period. The second derivative of the PWS with respect to time is denoted 2PWS herein. The average cardiac cycle waveforms represent the average cardiac cycle waveform at respective time points in the time period covered by the PWS. Thus, an initial step is to determine an average cardiac cycle waveform from a PWS. Techniques for determining an average cardiac cycle waveform from a PWS are described in the following section.

Determining Average Cardiac Cycle Waveforms

The averaging over multiple cardiac cycles is used to reduce or remove the noise in the resulting average to enable an improved analysis of reflected pulse waves and/or other characteristics of the cardiac cycle waveform. For a PWS that includes information about pulse changes/pulse waves at a measurement point on a body of a subject, reference points for each of the cardiac cycles to be smoothed are identified in the PWS. The reference point to be identified preferably relates to the initial up-flank of the pulse wave (i.e. the onset of the pulse wave), which should be free of influences of reflections and hence should be a stable reference point (i.e. not dependent on blood pressure changes). However it will be appreciated that a different reference point can be used if desired. Next, the times and amplitudes of the various occurrences of the reference points are used in order to compute an average cardiac cycle waveform.

In some embodiments, normal averaging of all cardiac cycle waveforms across the time window is used, for example as described in WO 2015/044010. That is, after aligning the individual cardiac cycle waveforms at the respective identified reference point, the amplitude values of the 2PWS at each 'lag time' from the identified reference point are averaged (e.g. the mean can be calculated) to form the average cardiac cycle waveform.

However, the 'normal averaging' described above does not allow for time-varying circumstances, i.e. where the blood pressure changes during the time period covered by the averaging process. Thus, in a more preferred approach, an averaging technique can be used that extends the averaging to allow for (linear) variation in time for each lag in the averaging procedure (where the lag, or lag time, is a time relative to the identified reference point for each cardiac cycle, e.g. the time relative to the identified a reference point for each cardiac cycle). This averaging technique is described in European patent application no. 20214268.3 filed on 15 Dec. 2020 in the name of Koninklijke Philips N.V. which is entitled "Method, apparatus and computer program product for analysing a pulse wave signal".

The flow chart in FIG. 4 shows an exemplary method for analysing a PWS obtained from a subject to determine an average cardiac cycle waveform. In some implementations, the processing unit 34 in the apparatus 30 can be configured to implement the method in FIG. 4. In other implementations computer readable code can be provided that causes a computer or the processing unit 34 to perform the method of FIG. 4 when the computer or processing unit 34 executes the code.

The PWS is received from a pulse wave sensor 32 located at a single measurement point on the subject and the PWS represents pulse wave measurements for a plurality of cardiac cycles (i.e. heart beats) of the subject. The method in FIG. 4 is described below with reference to a PWS in the form of a PPG signal, but it will be appreciated that the method can be applied to other forms of PWS. In some implementations, the method in FIG. 4 can be performed periodically or continuously on a PWS as it is received or measured from the subject. In some implementations, the method of FIG. 4 can operate on a windowed portion of a longer PWS, for example a 1-minute window of a PWS covering a time period of 1 hour. However, it should be appreciated that the method can be applied to a PWS having any desired length that covers any number of cardiac cycles. In the following description, references to operations or steps being performed on the PWS relates to performing those operations or steps on the part of the PWS of interest, e.g. a part corresponding to a 1-minute time period.

In a first step of the method, step 40, the PWS is analysed to identify cardiac cycles, and a respective reference point is identified for each cardiac cycle. The reference point is a point in each cardiac cycle that can be used in subsequent steps to 'align' the cardiac cycles and enable an average to be determined.

As described above with reference to FIG. 1, each cardiac cycle in an 'acceleration waveform' (the second derivative of the PWS with respect to time) can be considered to comprise five 'fiducial points' or 'reference points'. The a reference point marks the start of the direct pulse wave, which is the onset of the pulse wave (i.e. the pulse of blood caused by the beat of the heart) and the b point marks the end of the direct pulse wave. The e point marks the end of the systolic period (aortic valve closure), and for the purposes of this disclosure it is assumed that the c point marks the start of the reflected wave and the d point marks the end of the reflected wave. Preferably, in step 40 the reference point for each cardiac cycle is the onset of the pulse wave (the direct part of the pulse wave) which can be seen as the start of the systole phase—i.e. reference point a. However, it will be appreciated that in other embodiments, other ones of the reference points can be identified in step 40, or indeed a different reference point to reference points a to e shown in FIG. 1(*c*).

In the following, the signal corresponding to the first derivative of the PWS with respect to time is denoted '1PWS' and the signal corresponding to the second derivative of the PWS with respect to time is denoted '2PWS'. When described with reference to the specific example of a PPG signal, the 1PWS is also referred to as a 'velocity waveform' (v-PPG) and the 2PWS is also referred to as an 'acceleration waveform' (a-PPG).

Some embodiments of step 40 provide for the detection of the onsets of the pulse wave by detecting the local maxima in each cardiac cycle represented in the 2PWS. However, it can be seen in FIG. 1(*c*) that a double-differentiated PPG signal can be of low quality because of noise or quantization in the original PPG signal.

Figure 5:
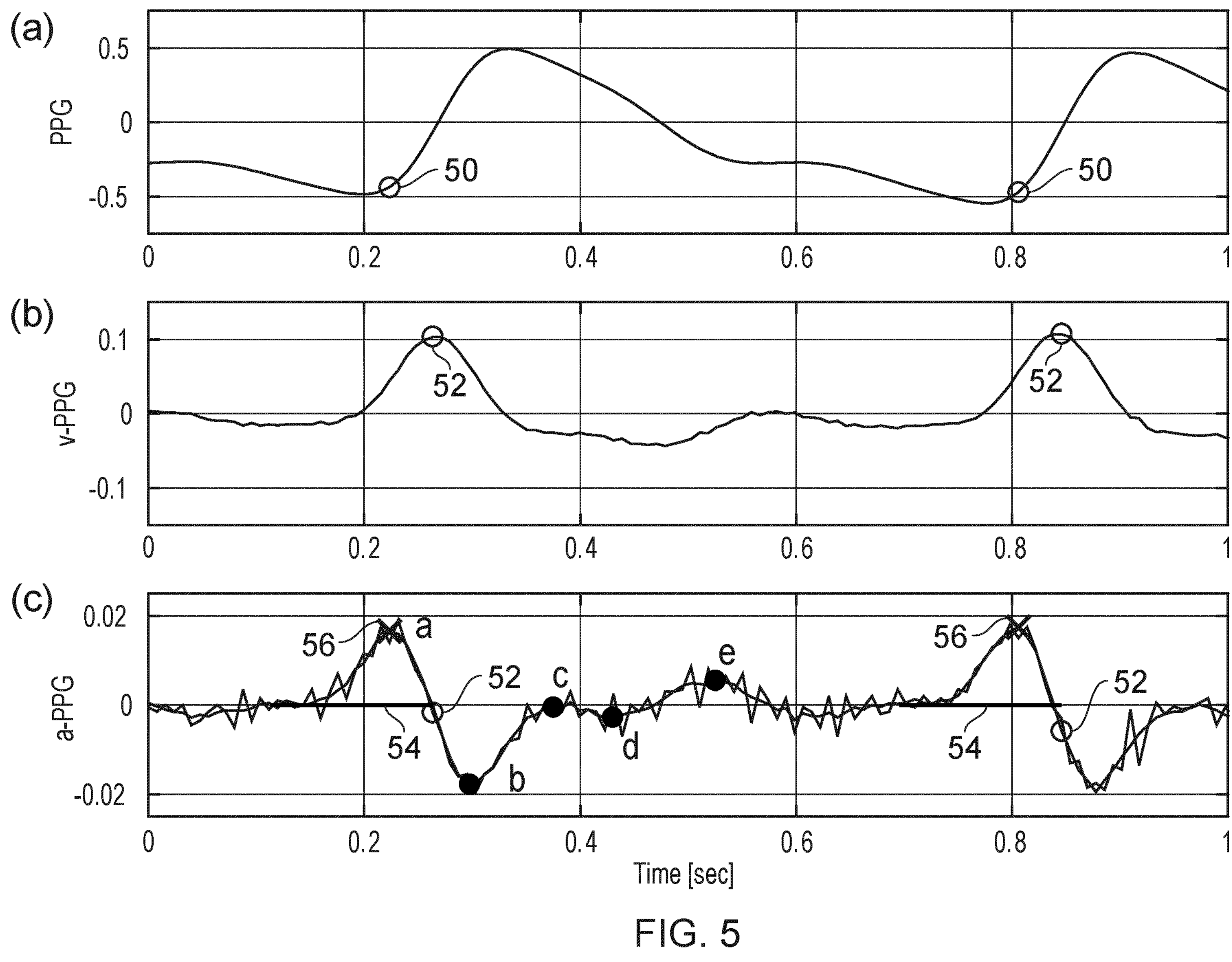
FIG. 5 shows a 1-second segment of a PPG signal, and FIGS. 5(*b*) and 5(*c*) show the first and second derivatives of the PPG signal respectively.

Therefore, in a more preferred implementation, the onset of the pulse wave is detected using a two stage process. FIG. 5(*a*) shows the same 1-second segment of the PPG signal shown in FIG. 1(*a*). FIG. 5(*b*) shows the first derivative of the PPG signal with respect to time (v-PPG), and FIG. 5(*c*) shows the second derivative of the PPG signal with respect to time (a-PPG). In FIG. 5(*a*), the onset of the pulse wave for the two cardiac cycles is indicated by the points labelled 50, and the aim of this embodiment is to identify these points. In the first stage, peak detection is performed on the first derivative of the PWS with respect to time (1PWS). It can be seen in FIG. 5(*b*) that the peaks in the v-PPG signal will correspond roughly to the steepest flank in the original PPG waveform (shown in FIG. 5(*a*)). The time-locations of the peaks detected in the v-PPG signal are labelled 52.

After detecting the maximum velocity peaks 52 in the 1PWS, then in the second stage narrowed (local) search windows are applied to the 2PWS (e.g. the a-PPG shown in FIG. 5(*c*)) based on the timing of each of the maximum velocity peaks 52, and the maximum peaks in those narrowed search windows on the 2PWS are detected. The narrowed search window can have a duration of 30-100 ms. These maximum peaks correspond to the desired a reference points, i.e. the onset of the pulse wave corresponding to the up-flank in the PWS signal. In the a-PPG waveform shown in FIG. 5(*c*), the narrowed search windows are indicated by the horizontal lines 54 that end at the timing of the detected velocity peaks 52. The maximum peaks identified in those narrowed search windows on the a-PPG waveform are labelled 56, and correspond to the desired a reference points.

Since the 2PWS can be noisy in case of poorly quantized signals, it can be beneficial to perform some smoothing prior to detection of the peaks in the 2PWS. This smoothing can be applied to the PWS before differentiation, applied to the 1PWS before peak detection is performed or applied to the 2PWS before peak detection is performed. In some implementations the smoothing can be achieved using by filtering, e.g. Savitzky-Golay filtering. The result of the smoothing process and differentiating a smoothed PWS/1PWS to determine the 2PWS can be seen by the smoothed line in FIG. 5(*c*).

In FIG. 5(*c*) the maxima/minima of the b, c, d and e waves are also shown for the first cardiac cycle. It can be seen that the c and d waves are very small (even in this best case situation) and will typically be very difficult to detect robustly. This illustrates the preference for the detection of the a reference point, but as noted above it would be possible to target the detection of other reference points in step 40. In the following, the detected a reference points for multiple cardiac cycles are used to perform an averaging of multiple cardiac cycles in order to determine an average cardiac cycle waveform.

Figure 6:
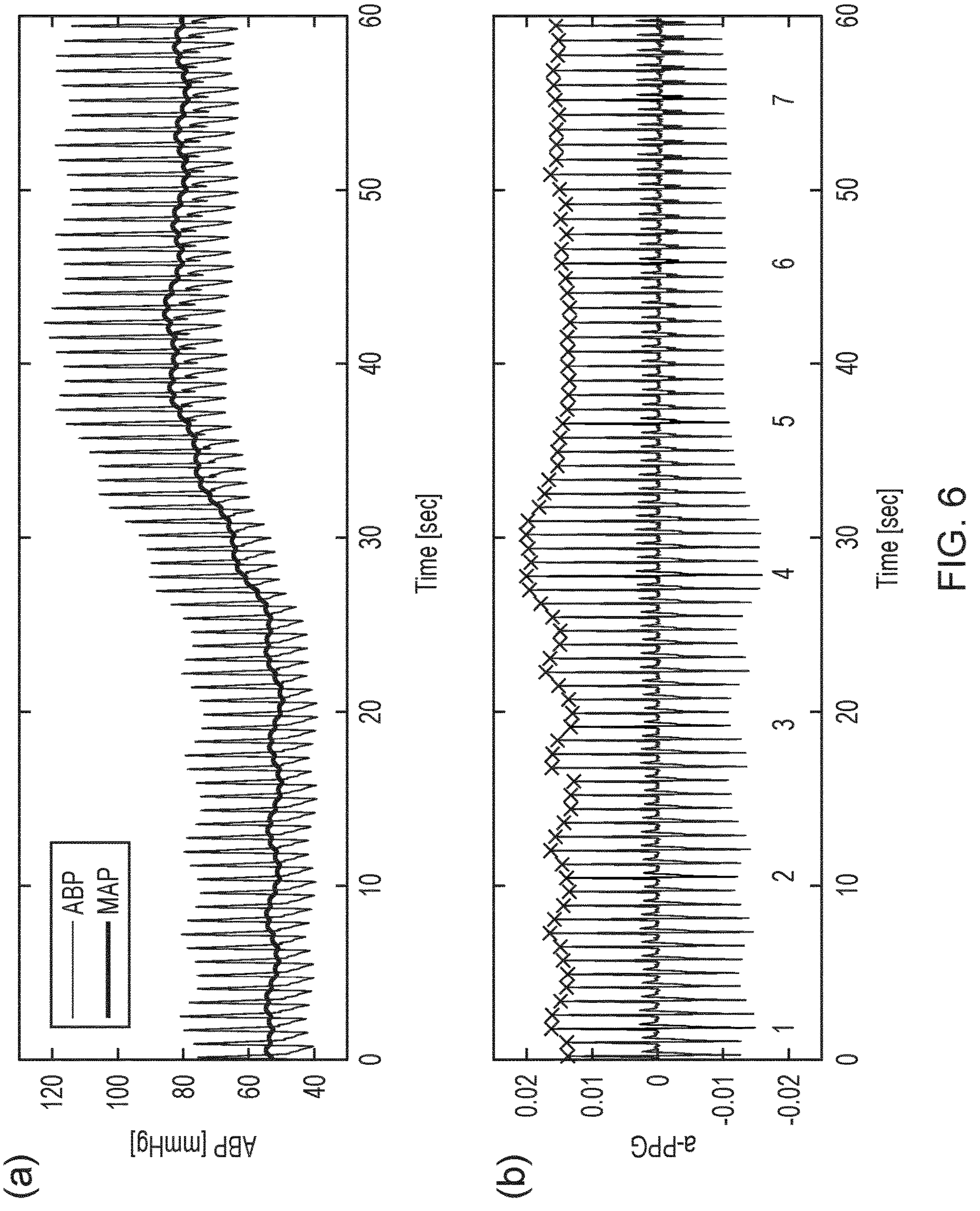
FIG. 6(*a*) shows a graph of arterial blood pressure in a 1-minute time window and FIG. 6(*b*) shows a graph of a second derivative of a pulse wave signal during the 60-second time window.

Next, in steps 42, 44 and 46, an averaging technique is applied to the PWS to determine an average cardiac cycle waveform for one or more timing points in the PWS. Steps 42, 44 and 46 are described below with reference to the exemplary 2PWS (in the form of an a-PPG) shown in FIG. 6(*b*). The 2PWS in FIG. 6(*b*) is derived from a PPG signal covering a 1-minute time period for a particular subject. This 1-minute time period covers 74 cardiac cycles of the subject. The respective reference points identified in step 40 for each cardiac cycle in the a-PPG waveform are marked in FIG. 6(*b*). FIG. 6(*a*) shows measurements of the arterial blood pressure (ABP—the thin line) and mean arterial pressure (MAP—the thicker line) for the same subject and same time period that the a-PPG signal in FIG. 6(*b*) relates to. The ABP measurement is shown in FIG. 6(*a*) to provide context for the a-PPG waveform in FIG. 6(*b*), and it will be appreciated that an ABP measurement will typically not be available for a subject for which a single-spot PWS measurement is being obtained. It can be seen in FIG. 6(*a*) that there is an increase in the mean arterial pressure of the order of 40 mmHg between 20 and 40 seconds. In the a-PPG waveform (FIG. 6(*b*)) there is some visible change at around 30 seconds (e.g. high respiratory modulation of the a reference points from 0-30 seconds and low respiratory modulation of the a reference points from 30-60 seconds), and the averaging technique described herein can be used to identify and/or analyse the changes in the morphology of the a-PPG waveform over and/or throughout the 60-second window.

Figure 7:
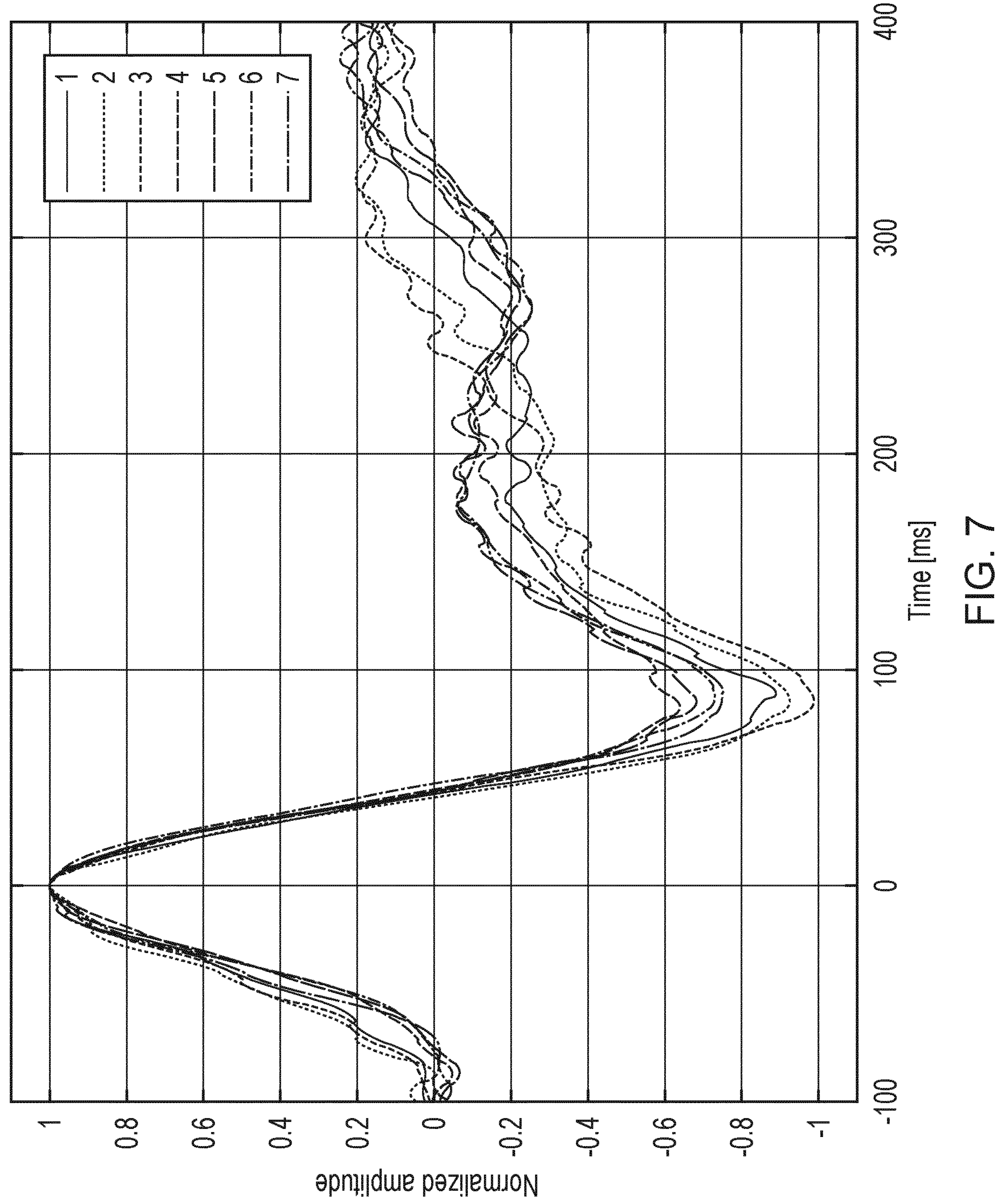
FIG. 7 is a graph showing a plurality of waveforms identified in the second derivative of the pulse wave signal overlaid with each other.

To show how the morphology of the a-PPG changes over the 60-second duration, FIG. 7 is a graph showing seven cardiac cycles from the a-PPG waveform of FIG. 6(*b*) overlaid with each other. The seven cardiac cycles included in FIG. 7 are labelled 1 to 7 in FIG. 6(*b*), and they are relatively evenly spaced through the 1-minute time window. It should be noted that these 7 cardiac cycles have been arbitrarily chosen from the cardiac cycles identified in FIG. 6(*b*) simply to provide a representation of how the cardiac cycle can change. In FIG. 7 the a-PPG waveforms for the 7 selected cardiac cycles are overlaid with the a reference points of each a-PPG waveform aligned at time t=0, and the respective a-PPG waveforms are normalised so that the amplitude of each a-PPG waveform at t=0 is the same (amplitude=1), and at other times the a-PPG waveforms have an amplitude that is usually in the range of −1 to 1. Each of the 7 waveforms shown in FIG. 7 are referred to as 'normalised' a-PPG waveforms herein, i.e. they are normalised around a common time point (e.g. reference point 'a' of each cardiac cycle in this example), with the amplitudes of the a-PPG waveforms matched at that reference point.

It can be seen in FIG. 7 that the complete morphology (after the a reference point) changes over time because of the blood pressure change. It can also be seen that it is very difficult to identify or analyse the waveforms separately, in part due to the noise in the second-derivative computation.

Since the pulse wave morphology can be constantly changing, as shown in the example of FIG. 7, simply applying an averaging to the multiple waveforms would lose the high-frequency information that is relevant for the analysis of the reflected pulse wave. Therefore, an averaging method is required where a linear change can be taken into account. The averaging technique disclosed herein is based on the technique in WO 2015/044010 with an extension to accommodate the linear change.

For describing the algorithm hereafter, a vector x is defined as the a-PPG data in a time window with size N. The reference points (which in the following worked example are the peak locations, the a reference points) of the waveform selection $\underline{x}$ are listed as a vector $\underline{p}$ that has a length $N_p$, where $N_p$ is the number of cardiac cycles/identified reference points. In the example of FIGS. 6 and 7, $N_p$ is 74. The waveform values at the detected peak locations are denoted by $\underline{x}_{(p)_j}$ where j=0, . . . , $N_p-1$ is the index of the peak in each heart cycle. The values from the peak locations will be denoted in short format later on as $$\underline{x}_{(\underline{p})_j} \triangleq (\underline{x}_p)_j. \tag{2}$$

where j=0, . . . , $N_p-1$ is the index of the peak.

The next step in the averaging process is to analyse the $N_p$ neighbouring samples (towards the left and right with respect to the initial peaks (the a reference points) and compute the average change (decrease) compared to the initial peak level. Similar to the peaks, the neighbouring locations with respect to the peak locations are defined in short format as:

$$\underline{x}_{(\underline{p})_j+\Delta_k} \triangleq \left(\underline{x}_{p+\Delta_k}\right)_j \tag{3}$$

where $\Delta_k$ is the lag index with respect to the peak locations, which can be either positive or negative valued.

For all neighbouring locations with respect to the peak locations which are inside the 1-minute window, the average level change (drop) is computed as:

$$\psi\Delta_k = \frac{1}{N} \sum_{\substack{j=0 \\ 0 \le [(\underline{p})_j + \Delta_k] < N_x}}^{N_p - 1} \frac{(\underline{x}_p)_j - (\underline{x}_{p+\Delta_k})_j}{(\underline{x}_p)_j}, \tag{4}$$

where N equals the number of averaged values that are in the region $[0 \ldots N_x - 1]$.

This means that N in the averaging procedure is not necessarily equal to the number of peaks $N_p$, and will be 1 or 2 smaller depending on whether some of the values $(\underline{p})_j + \Delta_k$ are outside the window with length $N_x$.

The computation of the model is done for several negative and positive values of $\Delta_k$, called iterations or repetitions. All the average values in the average model can be independently computed. Since only the average model values in the systole phase of the heart-cycle are of interest, bounds for the negative and positive values of $\Delta_k$ can be applied. For the negative values of $\Delta_k$ only negative values that are part of the start of the systole phase can be included. Since the peak location is very close to this start of the systole, the negative values of $\Delta_k$ can be limited to be equivalent to e.g. −0.1 seconds. For the positive values of $\Delta_k$, lags that are part of the remainder of the systole are included. Typical maximum positive values for $\Delta_k$ can be chosen to be equivalent to e.g. 0.4 seconds. The average normalised waveform $\underline{w}$ can now be computed for all lag indices $\Delta_k$ as:

$$(\underline{w})_{\Delta_k} = 1 - \psi_{\Delta_k}, \tag{5}$$

with $\psi_{\Delta_k}$ as computed by Equation (4).

Figure 8:
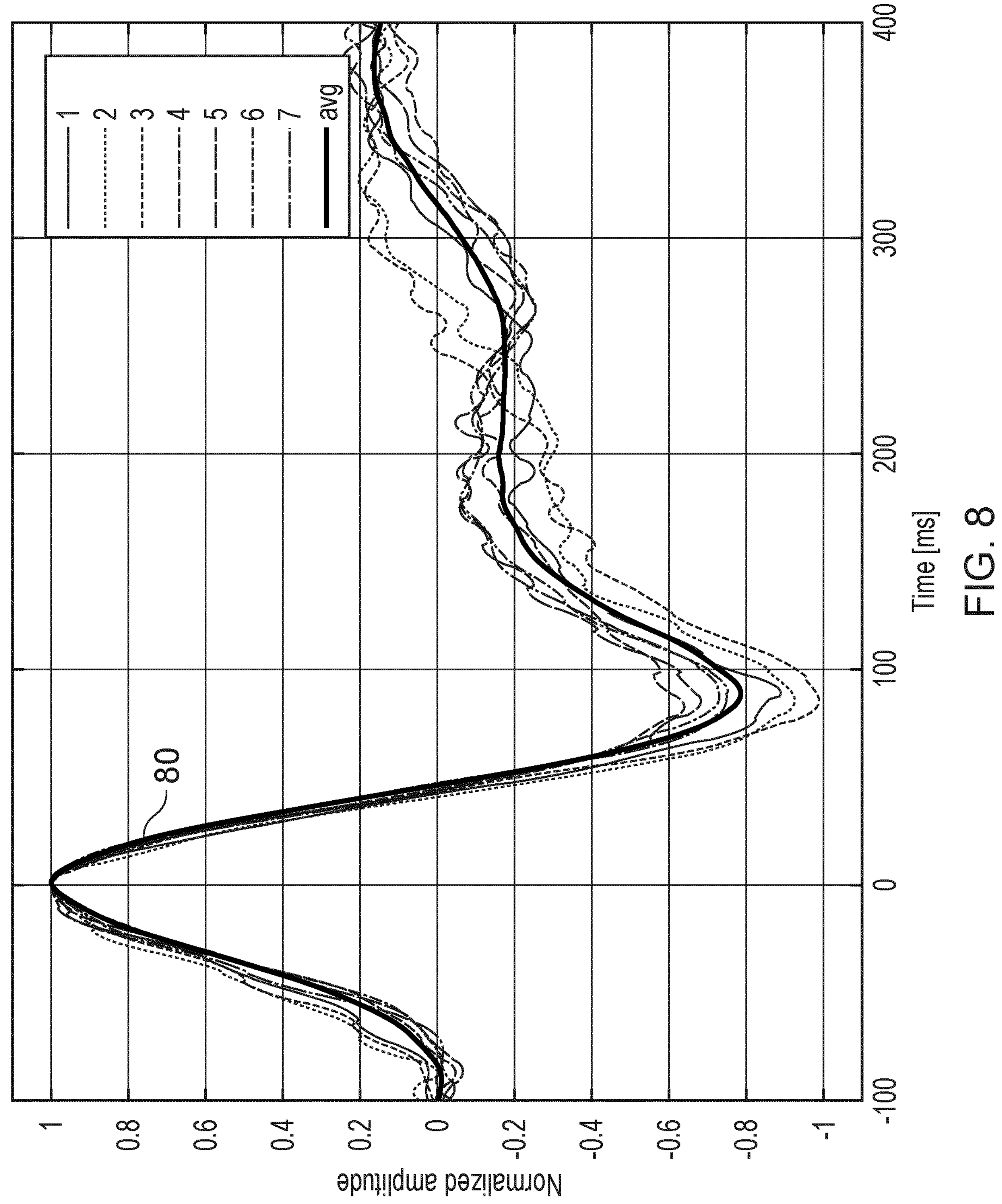
FIG. 8 is a graph showing a 0-th order average of the plurality of waveforms shown in FIG. 7.

FIG. 8 shows the average normalised waveform (the thicker line 80) overlaid on the seven cardiac cycles from the normalised a-PPG waveforms shown in FIG. 7. In effect, the average normalised waveform 80 from the above process is obtained by taking the average (mean) of each normalised cardiac cycle at each lag time value ($\Delta_k$) from time t=0. For example, the value of the average waveform 80 at time t=+100 ms is given by the average (mean) of the values of the individual normalised a-PPG waveforms at time t=+100 ms (i.e. normalised in time and amplitude relative to the identified a reference point for each cardiac cycle). This average waveform 80 can also be described as a 0-th order polynomial fit for the normalised a-PPG cardiac cycles.

However, as shown in FIG. 8, this average over the full 1-minute window is not a good fit for all of the normalised cardiac cycles in the full 1-minute window since the morphology of the waveform is varying over time.

Therefore, the above averaging procedure is generalised to accommodate time-varying situations by not simply computing the 0-th order average of the $N_p$ values at lag time $\Delta_k$, but a $1^{st}$ order or higher polynomial fit of the $N_p$ values at lag time $\Delta_k$. Since this polynomial fit, having order n (where n is equal to or greater than 0) will have time on the x-axis and the level drop values on the y-axis, the averaged (or curve fitted) level drop will also have a dependency on time for polynomial orders larger than 0. For each of the lag times $\Delta_k$, m+1 (m≤n) polynomial curve fit coefficients can be computed. These coefficients $a_0, \ldots, a_m$ can be computed in such a way to obtain a minimisation in the least-squares sense:

$$\arg\min_{a_0, \ldots, a_m} \sum_{\substack{j=0 \\ 0 \le [(\underline{p})_j + \Delta_k] < N_x}}^{N_p - 1} \left( \frac{(\underline{x}_p)_j - (\underline{x}_{p+\Delta_k})_j}{(\underline{x}_p)_j} - M^n_{j,\Delta_k} \right)^2, \tag{6}$$

where $$M^n_{j,\Delta_k}$$

is the linear fitting model:

$$M^n_{j,\Delta_k} = a_0 + a_1 \cdot [(\underline{p})_j + \Delta_k] + \ldots + a_m \cdot [(\underline{p})_j + \Delta_k]^n.$$

Next, based on the polynomial coefficients $a_0, \ldots, a_m$, the average level change (drop) can be computed directly via the linear fitting model $M^n_{j,\Delta_k}$ as:

$$\psi^n_{j,\Delta_k} = M^n_{j,\Delta_k}.$$

Figure 9:
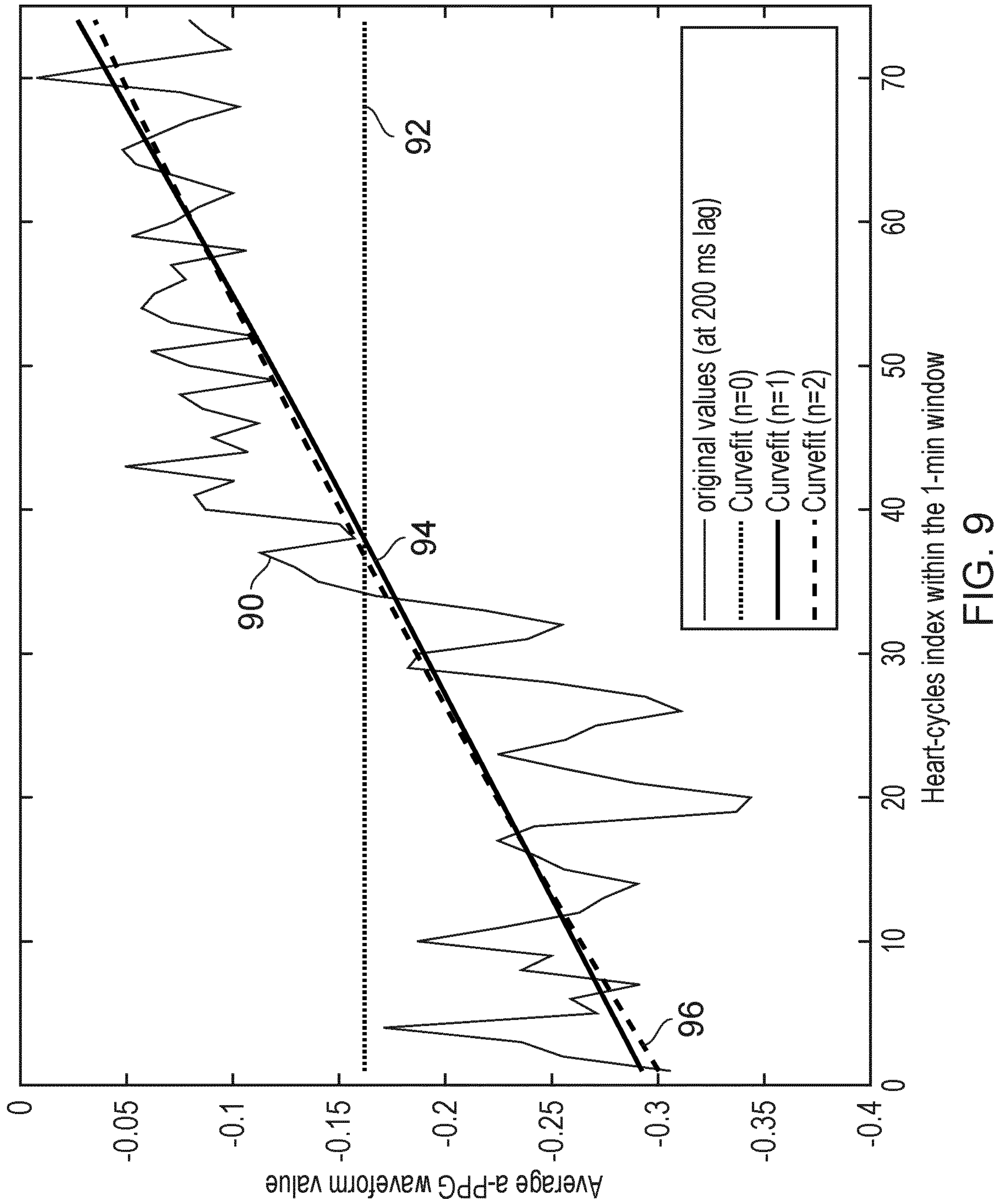
FIG. 9 is a graph showing values from the plurality of waveforms identified in the second derivative of the pulse wave signal at a particular lag time value from a common reference point, and three n-th order polynomial fits for the displayed values.

It can be seen that for n=0, we obtain the average level change (drop) as given by Equation (4) and via using Equation (5) we get the average fitting model as described in WO 2015/044010 and shown in FIG. 8, which will not depend on the sample index within the time window (e.g. the 1-minute window in this example). However, for n>0, the average fitting model will depend on the sample index within the time window. This is illustrated in FIG. 9, which shows the normalised a-PPG waveform values at a lag time of +200 ms with respect to the identified a reference points for the 74 cardiac cycles in the above example. The normalised a-PPG waveform values are indicated by line 90. FIG. 9 also shows the 0-th order average of the normalised a-PPG waveform values at lag time +200 ms (line 92—which corresponds to the conventional approach to just average (derive the mean) of all values at that time lag), the $1^{st}$ order average of the normalised a-PPG waveform values at lag time +200 ms (line 94), and the $2^{nd}$ order average of the normalised a-PPG waveform values at lag time +200 ms (line 96). Respective versions of FIG. 9 (i.e. respective fitted models) are determined for a range of lag time values.

Figure 10:
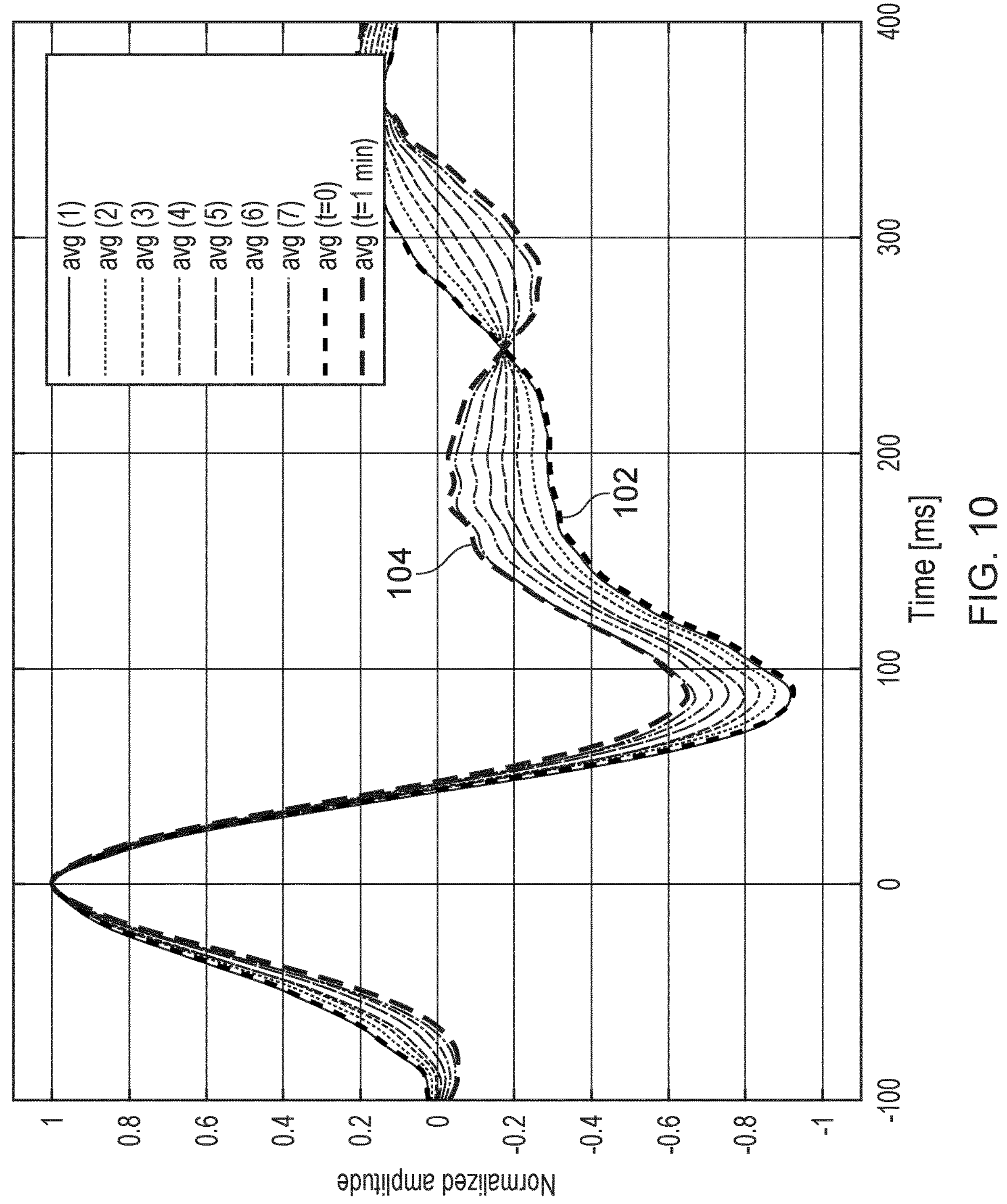
FIG. 10 is a graph showing $1^{st}$ order average waveforms for several time points during the 60-second time window.

The graph in FIG. 10 shows average normalised cardiac cycle waveforms for several time points in the a-PPG signal in FIG. 6(*b*) using the average (time-varying) fitted models for the range of lag time values for n=1. Thus, FIG. 10 shows the average waveform resulting from determining the $1^{st}$ order averages of the normalised a-PPG waveform values at a range of lag time ($\Delta_k$) values. Merely as an example, FIG. 10 shows the average waveform for time t=0 (labelled 102), time t=1 minute (labelled 104), and the average waveforms for the times corresponding to waveforms 1-7 labelled in FIG. 6(*b*).

It can be seen from a comparison of FIG. 9 to the values of the average cardiac cycle waveform in FIG. 10 at a lag value of +200 ms that the value at +200 ms for the averaged waveform for time t=0 is −0.3 (i.e. the $1^{st}$ order polynomial fit 94 has a value of −0.3 for t=0 (or the cardiac cycle with index 0)), whereas the value at +200 ms for the averaged waveform for time t=1 minute is approximately 0 (i.e. the 1$^{st}$ order polynomial fit 94 has an approximate value of 0 for t=1 minute (or the cardiac cycle with index 73))

The average cardiac cycle waveform for a selected time in the 1-minute time window can therefore be derived from the respective polynomial fit at each of the lag time values. In addition, it can be seen that all intermediate average results (for the times corresponding to the normalised a-PPG waveforms labelled 1 to 7 in FIG. 6(*b*)) at the different timings within the 1-minute window can also be computed. Therefore, by using an order n≥1, time-varying changes are accommodated in the averaging procedure. It should be noted that although n can be any integer value equal to or greater than 1, n=1 already gives good results in practice for a PWS representing a cardiac cycle in which the PWS is analysed over a relatively short time period and the underlying changes in the waveform are straightforward. If there are expected to be more substantial changes in the morphology over time, then n can be set to a value higher than 1.

Steps 42, 44 and 46 in FIG. 4 implement the above averaging technique as follows. In line with the above averaging technique, steps 42, 44 and 46 operate on a 'normalised 2PWS'. The normalised 2PWS is obtained by separately normalising each part of the 2PWS corresponding to a respective cardiac cycle identified in step 40 with respect to the amplitude of the 2PWS at the identified reference point for that cardiac cycle. That is, for a particular cardiac cycle identified in step 40, the amplitude of the 2PWS corresponding to that cardiac cycle is normalised around the amplitude of the 2PWS at the identified reference point for that cardiac cycle.

In step 42, for a first lag time value, $\Delta_k$, that is measured with reference to the identified reference points, an n-th order polynomial fit is determined for a first set of values of the normalised 2PWS. As noted above, n is equal to or greater than 1. The first set of values of the normalised 2PWS comprises the values of the 2PWS occurring the first lag time value from the reference point of each identified cardiac cycle. That is, in step 42, for a time lag value of X ms, the first set of values is the values of the normalised 2PWS that are X ms from each of the reference points identified in step 40. In the example shown in FIG. 9, the first set of values corresponds to the line 90. The n-th polynomial fit (with n≥1) determined in step 42 corresponds to line 94 for n=1 and line 96 for n=2.

In step 44, step 42 is repeated one or more times for one or more further time lag values. Thus, in step 44 one or more further iterations of step 42 are performed for one or more further lag time values to determine respective further n-th order polynomial fits 94, 96 for respective sets of values of the normalised 2PWS. Each of the respective sets of values of the normalised 2PWS comprises the values of the normalised 2PWS that occur the respective further lag time value from the reference point of each identified cardiac cycle. Thus, step 44 results in one or more versions of FIG. 9 being derived for the respective lag time value.

As noted below with reference to step 46, the number of times that step 42 is repeated determines the time-resolution of the averaged cardiac cycle waveform determined in step 46. The higher the number of times that step 42 is repeated, the higher the smoothness and resolution of the resulting average cardiac cycle waveform. In some embodiments, step 42 can be repeated for lag time values in the range −100 ms to +400 ms. It will be appreciated that an upper limit on the size of the lag time value range can be imposed by the heart rate of the subject. The lag time value range should cover one cardiac cycle or less (but enough of the cardiac cycle for pulse wave features such as the reflected pulse wave to be observed in the resulting average cardiac cycle waveform).

Next, in step 46, a first average cardiac cycle waveform is formed for a first time point in the time period covered by the PWS. The first average cardiac cycle waveform is formed from values of the plurality of n-th order polynomial fits 94, 96 at the first time point. Thus, for a time point Y in the time period covered by the PWS, the average cardiac cycle waveform is formed from the value at time point Y of the n-th order polynomial fit 94, 96 for the first set of values determined in step 42 (i.e. the value at time point Y of the n-th order polynomial fit 94, 96 for the first time lag value), and the respective values at time point Y of each of the further n-th order polynomial fits 94, 96 determined in step 44 (i.e. the values at time point Y of the n-th order polynomial fit 94, 96 for the further time lag values). In a specific example for a time point t=0 and n=1, the average cardiac cycle waveform is formed from the values of the 1$^{st}$ order polynomial fit 94 for each lag time value. Step 46 can result in, for example, an average cardiac cycle waveform 102, 104 as shown in FIG. 10.

Determining a Blood Pressure Change

As noted above, the described techniques avoid the use of multiple fiducial point detection in the computation of a surrogate blood pressure measurement by computing a surrogate blood pressure measurement from a morphology change of the average cardiac cycle waveform. In particular, a relative blood pressure change can be determined from an absolute value of a change in morphology across two average cardiac cycle waveforms determined as described above, and a direction of the morphology change.

Figure 11:
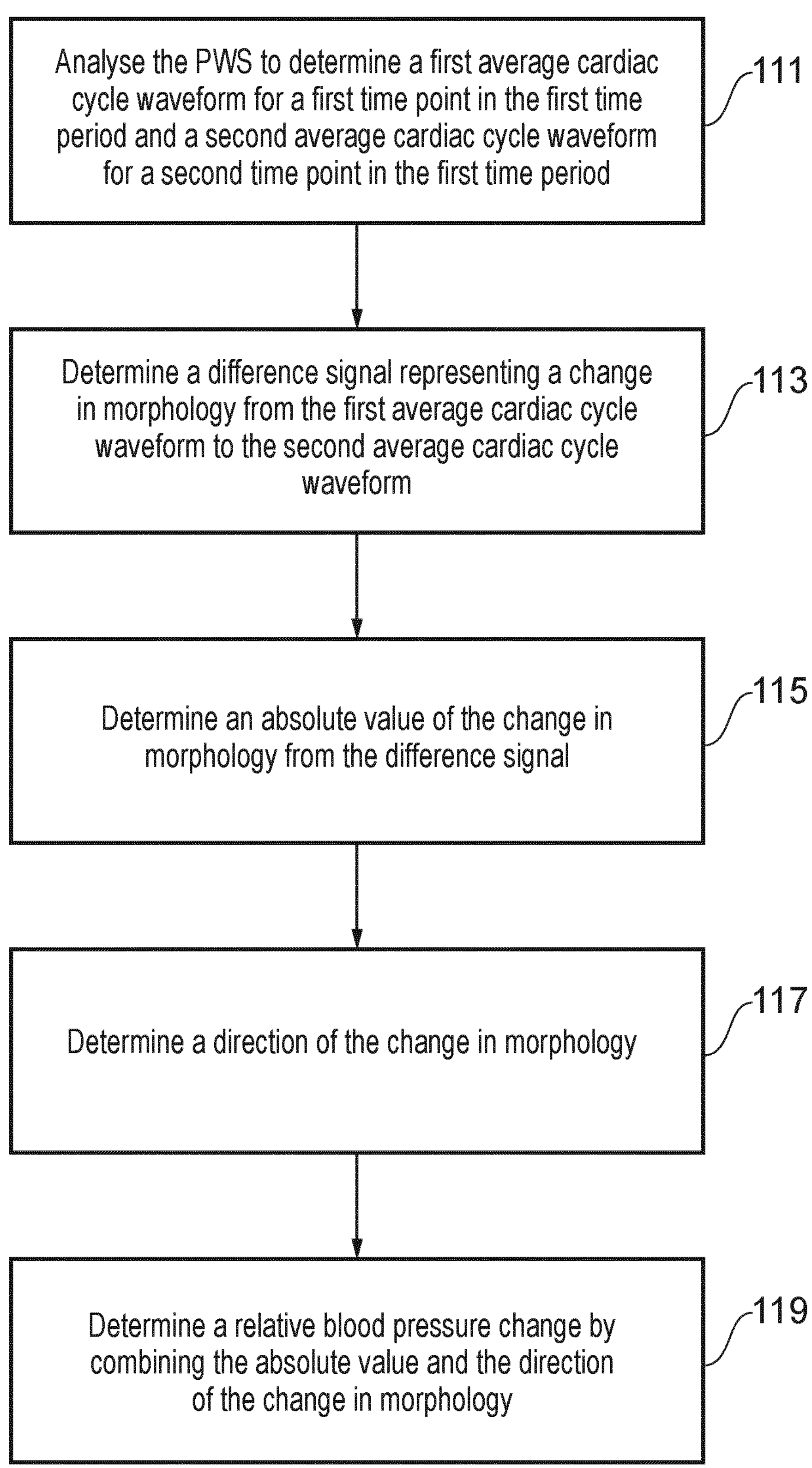
FIG. 11 is a flow chart illustrating a method for analysing a pulse wave signal obtained from a subject to determine an indication of the blood pressure or a change in blood pressure.

The flow chart in FIG. 11 shows an exemplary method for analysing a PWS obtained from a subject to determine an indication of the blood pressure or a change in blood pressure of the subject. In some embodiments, the processing unit 34 in the apparatus 30 can be configured to implement the method in FIG. 11. In other embodiments computer readable code can be provided that causes a computer or the processing unit 34 to perform the method of FIG. 11 when the computer or processing unit 34 executes the code.

Step 111 represents the initial step of analysing the PWS to determine a first average cardiac cycle waveform for a first time point in the first time period and a second average cardiac cycle waveform for a second time point in the first time period. Step 111 can be performed by taking the 'normal average' of the cardiac cycle waveforms across the time window as described in WO 2015/044010. Alternatively, and in more preferred embodiments, step 111 is performed as described above with reference to FIG. 4.

In these embodiments, step 111 can comprise the following sub-steps. In sub-step (i) the PWS is analysed to identify a plurality of cardiac cycles and a respective reference point for each identified cardiac cycle. In sub-step (ii), 2PWS is determined as a second derivative with respect to time of the PWS. In sub-step (iii), a normalised 2PWS is determined by, for each part of the 2PWS corresponding to a respective identified cardiac cycle, normalising said part of the 2PWS with respect to the amplitude of the 2PWS at the identified reference point for said cardiac cycle. In sub-step (iv), for a first lag time value, an n-th order polynomial fit is determined for a first set of values of the normalised 2PWS. The first set of values of the normalised 2PWS comprises the values of the normalised 2PWS occurring the first lag time value from the reference point of each identified cardiac cycle. n is equal to or greater than 1. In sub-step (v), one or more further iterations of sub-step (iv) are performed for one or more further lag time values to determine respective further n-th order polynomial fits for respective sets of values of the normalised 2PWS. A respective set of values of the normalised 2PWS comprises the values of the normalised 2PWS that occur the respective further lag time value from the reference point of each identified cardiac cycle. Finally, in sub-step (vi), a first average cardiac cycle waveform for a first time point in the first time period is formed. The first average cardiac cycle waveform is formed from values of the plurality of n-th order polynomial fits at the first time point. A second average cardiac cycle waveform for a second time point in the first time period, wherein the second average cardiac cycle waveform is formed from values of the plurality of n-th order polynomial fits at the second time point.

Thus, the two average cardiac cycle waveforms can be determined from a second derivative of a PWS (2PWS) that comprises pulse wave measurements for a number of cardiac cycles of the subject in a particular time period.

The particular time period covered by the PWS can be, for example, one minute, but the time period can have different durations, for example 30 seconds, 2 minutes, 5 minutes, etc. This particular time period is referred to as a 'frame'. In practical applications, the blood pressure measurements can be computed continuously over time, so the PWS can be iteratively analysed over frames that progress over time, where subsequent frames can partially overlap (e.g. 50 seconds overlap between frames of 1 minute duration). A sample (lag) in the average cardiac cycle waveform for the beginning of the time period is denoted:

$$\psi^n_{0,\Delta_k}(k)$$

where '0' is the index of the first cardiac cycle in the particular time period (frame), 'n' is the order of the averaging procedure and '$\Delta_k$' is the lag time in the single-cycle waveform. The variable κ is the frame-index. Similarly, a sample (lag) in the average cardiac cycle waveform at the end of the 1-minute averaging window is denoted:

$$\psi^n_{(N_p-1),\Delta_k}(k)$$

where $N_p-1$ equals the index of the least heart-cycle ($N_p=74$).

Thus, according to equations (9) and (10), the first average cardiac cycle waveform can be targeting the first cardiac cycle in the time period covered by the PWS, and the second average cardiac cycle waveform can be targeting the last cardiac cycle in the time period. However, it is possible for either or both of the first average cardiac cycle waveform and the second average cardiac cycle waveform to correspond to different cardiac cycles in the time period. It is alternatively possible to only compute the first average cardiac waveform at a first time point in the time period covered by the PWS as determined in step 46. In some embodiments, a second average cardiac cycle waveform can be formed for a second time point in the time period covered by the PWS. The second average cardiac cycle waveform can be formed in the same way as the first average cardiac cycle waveform determined in step 46. As an example, one of the first time point and the second time point can be at or near to the start of the PWS, and the other one of the first time point and the second time point can be at or near to the end of the PWS, similarly as in equations (9) and (10). In further embodiments, one or more further average cardiac cycle waveforms can be determined for respective time points in the time period covered by the PWS.

In step 113, a difference signal is determined from the first average cardiac cycle waveform and the second average cardiac cycle waveform. The difference signal represents a change in morphology from the first average cardiac cycle waveform to the second average cardiac cycle waveform.

In particular, the approach to determining the average cardiac cycle waveforms described above with reference to FIG. 4 enables average (second derivative) waveforms to be determined within a long time window, and this time-varying change of this average waveform can be modelled across this long window. Due to this time dependency property of the average waveform, the average change in the waveform across this long window can be computed. This can be done by simple subtraction, as follows:

$$\Delta\psi^n_{\Delta_k}(k) = \psi^n_{(N_p-1),\Delta_k}(k) - \psi^n_{0,\Delta_k}(k)$$

where $$\Delta\psi^n_{\Delta_k}$$

is the average change in morphology for lag $\Delta_k$ from the first cardiac cycle with index 0 in the long averaging window up to the last heart cycle with index ($N_p-1$) in the long averaging window.

In some embodiments, the difference signal resulting from step 113 comprises respective difference samples for a plurality of lag time values measured with respect to a respective reference point for the first average cardiac cycle waveform and the second average cardiac cycle waveform. The reference point can be the onset of a pulse wave of the subject, i.e. the 'a' fiducial point shown in FIG. 1. A difference sample for a particular lag time value can be the difference between the (the amplitude of the) first average cardiac cycle waveform at the particular lag time value and the (the amplitude of the) second average cardiac cycle waveform at the particular lag time value.

The basis for the blood pressure surrogate metric is the morphology change as computed by Equation (11). Hence, this morphology change can be correlated (and analysed) for each of the lags $\Delta_k$ in this metric with a reference blood pressure variation across the time period.

As a 'gold' reference for blood pressure, an ABP signal acquired intravenously from a subject is used to compute a (linear) trend in the MAP during a 5-minute window, by computing a linear regression within the 5-minute window. The MAP can be computed by using a second order Butterworth low-pass filter to compute the mean of the ABP data, with the filter having a cut-off frequency of, e.g., 0.025 Hz. A ΔMAP value can be computed based on the linear trend parameter that reflects the amount of change of MAP within the averaging windows. The relative BP change can then be computed as:

$$\Delta R_{MAP}(\kappa) = \frac{\Delta MAP(\kappa)}{MAP(\kappa)} \tag{12}$$

where $\Delta MAP(\kappa)$ is the change in MAP (in mmHg) and $MAP(\kappa)$ is the average MAP (also in mmHg) within the averaging window and where $\Delta MAP(\kappa)$ is obtained using a curve-fit procedure using the data within the averaging window.

The changes in morphology (difference signal) from Equation (11) can then be correlated (for each lag and each sliding window with a shift of 20 seconds) with the reference blood pressure change $\Delta R_{MAP(\kappa)}$ as given in Equation (12). Next, the correlation coefficient $r_{\Delta k}$ can be computed for each lag with index $\Delta_k$ as follows:

$$r_{\Delta_k} = \frac{\sum_{\kappa} \Delta R_{MAP}(\kappa) \cdot \Delta\psi^n_{\Delta_k}(\kappa)}{\sqrt{\sum_{\kappa} \Delta R^2_{MAP}(\kappa)} \sqrt{\sum_{\kappa} \left(\Delta\psi^n_{\Delta_k}(\kappa)\right)^2}}. \tag{13}$$

The computation of the correlation coefficients $r_{\Delta k}$ can be done for each lag $\Delta_k$. The mean values in $\Delta R_{MAP(\kappa)}$ and $$\Delta\psi^n_{\Delta_k}$$

do not have to be compensated since these modalities can already be assumed to be free of offset since they are computed via a difference computation.

Figure 12:
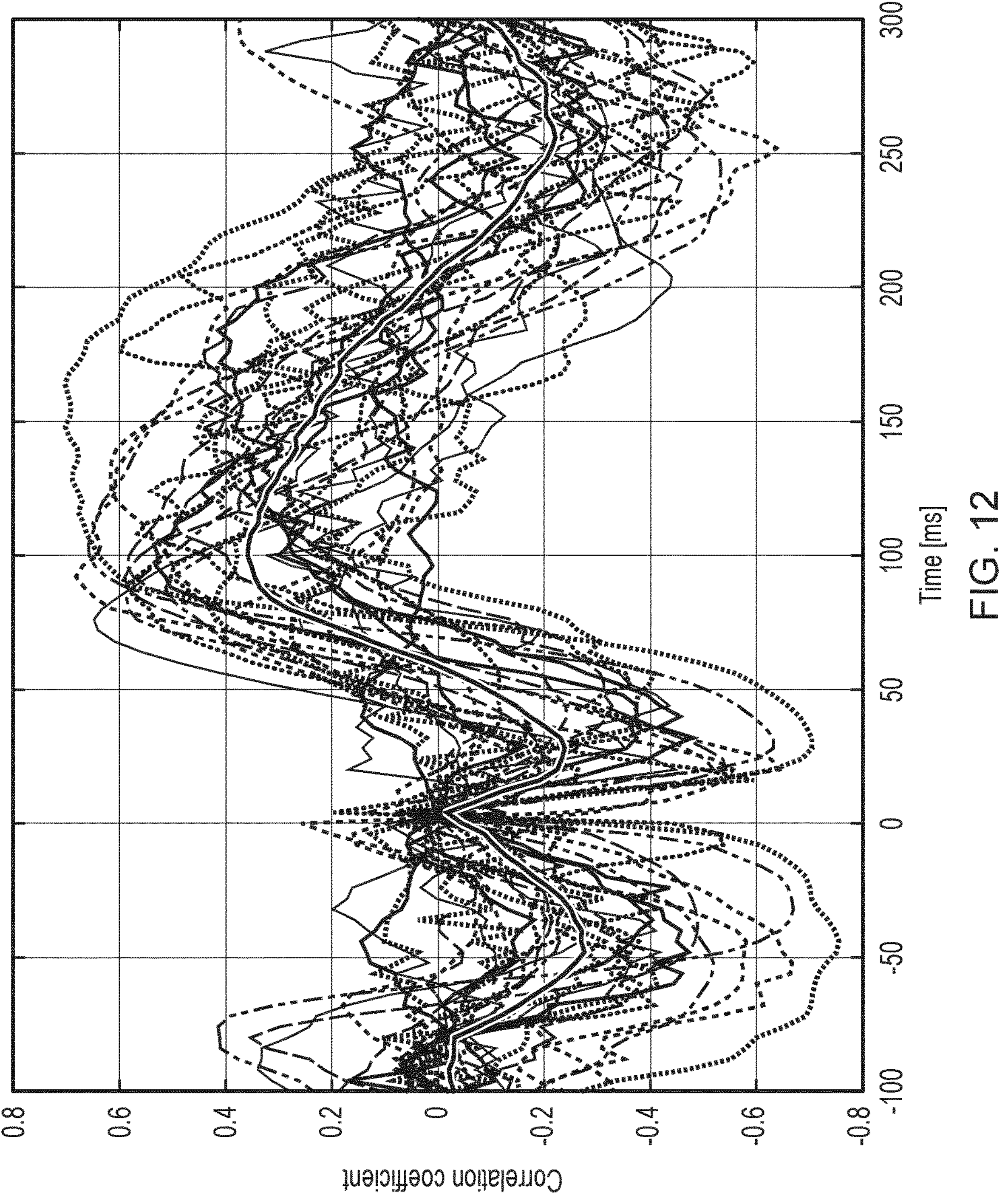
FIG. 12 is a graph illustrating correlation for a number of subjects between relative blood pressure change and a difference signal.

The result of this correlation is shown in FIG. 12 for each of 29 different subjects, with the average shown as a thick black curve. Thus, FIG. 12 shows the correlation coefficients for each subject as a separate line. Each line in FIG. 12 shows, for a particular subject, the correlation between the relative blood pressure changes (derived from a direct ABP measurement) and the respective difference signal for that subject for different lag times $\Delta_k$. As can be seen from FIG. 12, the individual subjects show very different results in the correlation. On the other hand, there are also similarities. The first is that the correlation is poorly defined at the reference point (at 0 ms lag time). The reason for this is that there cannot be any morphology change for this lag-time since the reference point always equals a unity value (by definition). The second similarity is that the lags that are close to the reference point at 0 ms are negatively correlated with the MAP change. This means that, typically, an increasing MAP leads to narrowing of the a-wave in the a-PPG signal. This can also be seen in the example of FIG. 10, where the a-wave becomes narrower in the course of the 1-minute window (especially from −100 ms up to 0 ms). This could relate to some heart properties, e.g. heart contractility, since it is known that the stroke volume (via cardiac output) directly relates to MAP. The third similarity is that in the middle systole period (e.g. beyond 75 ms up to 200 ms), the values in the morphology change positively correlate with the MAP change. This may be caused by the reflections in the arterial tree which are arriving earlier at the finger location (where the PWS sensor 32 is located for these subjects) for increasing MAP values. Also increases in b-wave amplitudes are known to be increasing for increasing blood pressures (i.e. negative valued b-points become less negative or even positive). This increase of the b-point values are probably caused by earlier return of reflected waves. The last similarity is that there is a general trend that in the late systole period, the values of the morphology change again negatively correlate with the MAP change. This may relate to the shift of timing of reflected waves. If for an increase in blood pressure the reflected waves have arrived earlier, there will also be a drop in the a-PPG waveform that occurs earlier after the reflected waves have passed.

Returning to FIG. 4, after determining the difference signal in step 113, in step 115 an absolute value of the change in morphology is determined from the difference signal. In some embodiments, the absolute value can be determined as the sum of the magnitude of the difference samples for the plurality of lag time values, for example lag time values from 0 ms to 300 ms.

Since from FIG. 12 there seems to be a blood pressure influence on the entire range of lags (i.e. −100 ms up to 300 ms with respect to the onset of the pulse wave, the ‘a’ fiducial point), the set $\mathcal{K}$ is defined to include all these lags. Thus, the set $\mathcal{K}$ can include the lags corresponding to the full systole phase of the cardiac cycle. The absolute value of the change of the morphology within a frame $\kappa$ can be computed as:

$$\Delta\Psi(\kappa) = \sum_{\Delta_k \in \{\mathcal{K}\}} \left|\Delta\psi^n_{\Delta_k}(\kappa)\right|, \tag{14}$$

where $\mathcal{K}$ is the range of lag times over which the morphology change is to be computed (e.g. −100 ms to 300 ms).

Instead of normalizing the morphology change in Equation (14) by the time-duration specified by the lags $\mathcal{K}$, in some embodiments a different normalisation can be performed that also takes into account the exact morphology of the pulse wave. The normalised change of morphology can be computed as:

$$\Delta\tilde{\Psi}(\kappa) = \frac{\Delta\Psi(\kappa)}{\Psi(\kappa)}, \tag{15}$$

where the normalization value $\Psi(\kappa)$ is computed as:

$$\Psi(\kappa) = \sum_{\Delta_k \in \{\mathcal{K}\}} \frac{1}{2} \cdot \left|\psi^n_{N_p-1,\Delta_k}(\kappa) + \psi^n_{0,\Delta_k}(\kappa)\right|. \tag{16}$$

In the normalisation value of Equation (15), the energy in the average wave is used and the trend information in the window is discarded. Furthermore, the values $\Delta\Psi(\kappa)$ and $\Psi(\kappa)$ are both positive valued. Hence, also the resulting normalised absolute morphology change $\Delta\tilde{\Psi}(\kappa)$ is positive valued.

Next, in step 117, a direction of the change in morphology is determined. Because the morphology change metric of Equation (15) and step 115 is positive-valued, the direction of blood pressure changes cannot be detected, and an extension of the relative blood pressure surrogate metric is introduced as follows:

$$\Delta\hat{R}_{morph}(\kappa) = \underbrace{\hat{s}(\kappa)}_{sign} \cdot \underbrace{\Delta\tilde{\Psi}(\kappa)}_{\%\,change}, \tag{17}$$

where $\hat{s}(\kappa)$ will be a sign estimation, i.e. the indication of the direction of the change in morphology.

In some embodiments, the direction of the change in morphology is determined in step 117 by analysing a pulse arrival time (PAT) signal for the subject during the first time period to determine a relative PAT change from the first time point to the second time point. The direction of the change in morphology is determined as the direction of the relative PAT change. As is known, the PAT is measured as the time interval from the R-peak on an ECG signal and the arrival of that pulse in a peripheral body location, such as the wrist or finger. Thus, to obtain the PAT for the subject, the PWS sensor 32 is placed at a peripheral body location, and an ECG sensor is provided to measure the electrical activity of the heart. The ECG signal from the ECG sensor and the PWS signal are analysed to determine the PAT for the subject.

In alternative embodiments, the direction of the change in morphology is determined in step 117 using the difference signal. In particular, the direction of the change can be determined in step 117 by determining the sum of the difference samples for a subset of the plurality of lag time values, and determining the direction of the change in morphology as the sign of the sum of the difference samples. In some embodiments, the subset of the plurality of lag time values can be lag time values from 75 milliseconds to 150 milliseconds after the onset of the pulse wave (i.e. the 'a' point). This is explained further below.

Since it has been seen above with reference to FIG. 12 that there is a strong positive correlation for the lag times ranging from 75 ms up to 150 ms, the sign $\hat{s}(\kappa)$ can be estimated by computing:

$$\hat{s}(\kappa) = \mathrm{sgn}\left\{\sum_{\Delta_k \in \{\mathcal{L}\}} \Delta\psi^n_{\Delta_k}(\kappa)\right\} \tag{18}$$

where $\mathcal{L}$ is the set of lag times that are taken into account for the sign estimation. It is useful to use the lag times that are clearly influenced by the reflection waves, i.e. in the range from 75 up to 150 ms. It should be noted that the metric $\Delta\hat{R}_{morph}(\kappa)$ is not a calibrated surrogate blood pressure metric, since the amount of morphology change will still depend on dynamic vascular properties.

Finally, in step 119, the relative blood pressure change is determined by combining the absolute value of the morphology change determined in step 115 and the direction of the change in morphology determined in step 117. The absolute value and the direction of the change (sign) can be combined according to Equation (17) to determine the relative blood pressure change. That is, the absolute value and the direction of the change in morphology can be multiplied together to determine the relative blood pressure change.

Determining an Absolute Blood Pressure

In further embodiments, an absolute blood pressure value can be determined from the relative blood pressure change. In particular, the relative blood pressure change determined in step 119 can be integrated with respect to time to determine an estimate of blood pressure of the subject (i.e. an absolute blood pressure value).

To avoid or reduce integration drifts in the estimation of the absolute blood pressure, at regular moments a calibration of the absolute blood pressure can be performed using another measurement of blood pressure, for example one obtained using oscillometric measurement techniques. Between the oscillometric measurements, the integral of the relative blood pressure change summed to the initial oscillometric value provides the surrogate absolute blood pressure measurement.

Thus, at a time point where a calibration blood pressure measurement is obtained, for example using an oscillometric measurement technique, the absolute blood pressure surrogate $\hat{MAP}(\kappa)$ is set to the calibration (e.g. oscillometric) blood pressure measurement at time instant $\kappa=c$:

$$\Delta M\hat{A}P(\kappa) = MAP(\kappa), \tag{19}$$

where $MAP(\kappa)$ is the calibration blood pressure measurement.

Next, iterative integration is performed using the next frames with index $\kappa>c$ to estimate new values of $\hat{MAP}(\kappa)$:

$$M\hat{A}P(\kappa) = M\hat{A}P(\kappa-1) + \frac{B}{N_x}\cdot\Delta M\hat{A}P(\kappa), \tag{20}$$

where the factor $B/N_x$ is the normalisation to make the integration independent of the averaging technique using a window length of $N_x$ with B samples overlap. $\Delta\hat{MAP}(\kappa)$ is the relative MAP change (within the window of $N_x$ samples), and is obtained using the surrogate relative blood pressure change determined in step 119 according to:

$$\Delta M\hat{A}P(\kappa) = QI(\kappa)\cdot\Delta\hat{R}_{morph}(\kappa)\cdot M\hat{A}P)(\kappa-1). \tag{21}$$

This gives:

$$M\hat{A}P(\kappa) = \left(1 + \frac{B}{N_x}\cdot QI(\kappa)\cdot\Delta\hat{R}_{morph}(\kappa)\right)M\hat{A}P(\kappa-1). \tag{22}$$

As can be seen, the quality index, $QI(\kappa)$, is a weighting factor that indicates the measure of quality for the relative blood pressure change as computed via Equation (17). The QU has a value in the range from 0 to 1. When the quality of the relative blood pressure change is poor, the value of $QI(\kappa)$ will be close to zero and the integration will not be disrupted by this poor quality. As a preferred embodiment, this measure of quality can be computed from the 'goodness of fit' of the first and second average cardiac waveform (as computed by Equation (9) and Equation (10)) on the plurality of cardiac cycle waveforms in PWS. For example, it can be computed as:

$$QI(\kappa) = \frac{\Psi(\kappa)}{\Psi(\kappa) + \gamma\sum_{\Delta_k \in \{\mathcal{K}\}} \sigma^n_{\Delta_k}(\kappa)}, \tag{23}$$

where $$\sigma^n_{\Delta_{b=k}}(\kappa)$$

is computed as:

$$\sigma^n_{\Delta_k}(\kappa) = \frac{1}{N_p}\sqrt{\sum_{j=0}^{N_p-1}\left(\left(\underline{x}_p + \Delta_k\right)_j(\kappa) - \psi^n_{j,\Delta_k}(\kappa)\right)^2} \quad (24)$$

and where $\gamma$ is a parameter that determines the sensitivity of the quality index value on the suppression of the integration. Smaller values of will lead to a lower sensitivity and smaller effect of the quality index value on the integration procedure. It was found that $\gamma=2$ gives good results. The measure of quality as defined by Equation (23) is bounded by $0 \leq QI(\kappa) \leq 1$.

It can be seen in Equation (22) that the surrogate absolute blood pressure measurement is computed recursively by using a reference point and continuous integration of the MAP-change estimate by exploiting the change in morphology and the quality index. The quality index can be used to avoid integration of erroneous estimated changes; more specifically, in Equation (21), the quality index is used as a weighting factor for the integration. For a poorer quality index, the contribution of the morphology change to the integrated value will be smaller.

Figure 13:
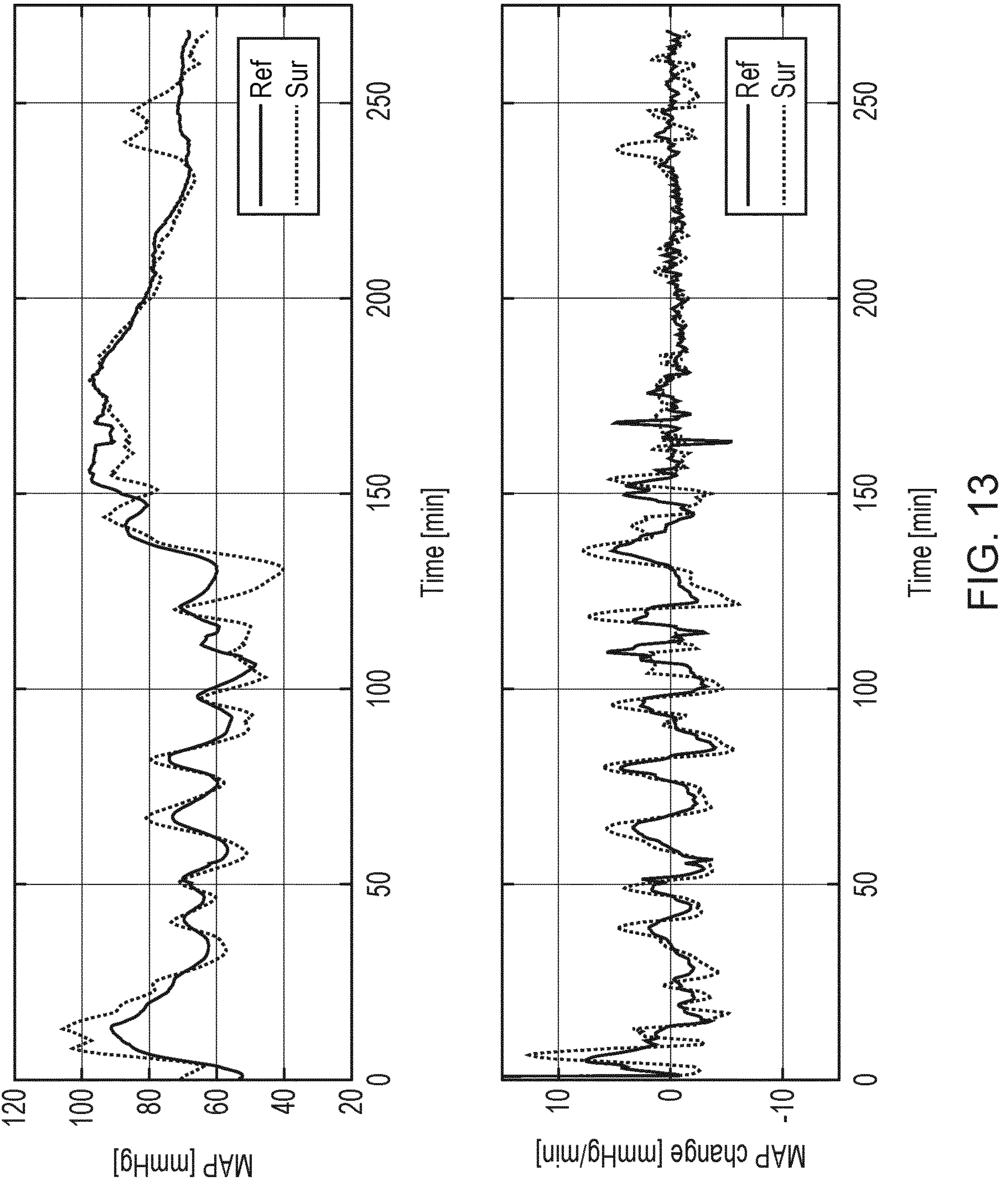
FIG. 13 is a pair of graphs illustrating estimates of absolute MAP and MAP change for a subject against reference MAP measurements.

FIG. 13 shows an exemplary result of this absolute surrogate MAP estimation together with reference MAP measurements for a test subject. FIG. 13(*a*) shows the estimated and reference absolute surrogate MAPs over a time period of approximately 270 minutes. FIG. 13(*b*) shows the estimated and reference relative surrogate MAPs (i.e. MAP change) over the same time period. The estimated absolute and relative surrogate MAPs are labelled 'Sur' in FIGS. 13(*a*) and (*b*) respectively, and the reference MAP and MAP change measurements are labelled 'Ref' in FIGS. 13(*a*) and (*b*) respectively. For the absolute surrogate estimation, it is possible to apply only a single calibration at t=0 minutes, where the value is set to a calibration blood pressure of 70 mmHg. Also shown in FIG. 13(*b*) is the (relative) MAP change (in mmHg/min) obtained via differentiation of the surrogate MAP estimate in FIG. 13(*a*). Again, the surrogate MAP change can be compared to the reference MAP change. This relative change obtained via differentiation of the surrogate is closely related to the percentage change $\Delta\hat{R}_{morph}(\kappa)$.

Figure 14:
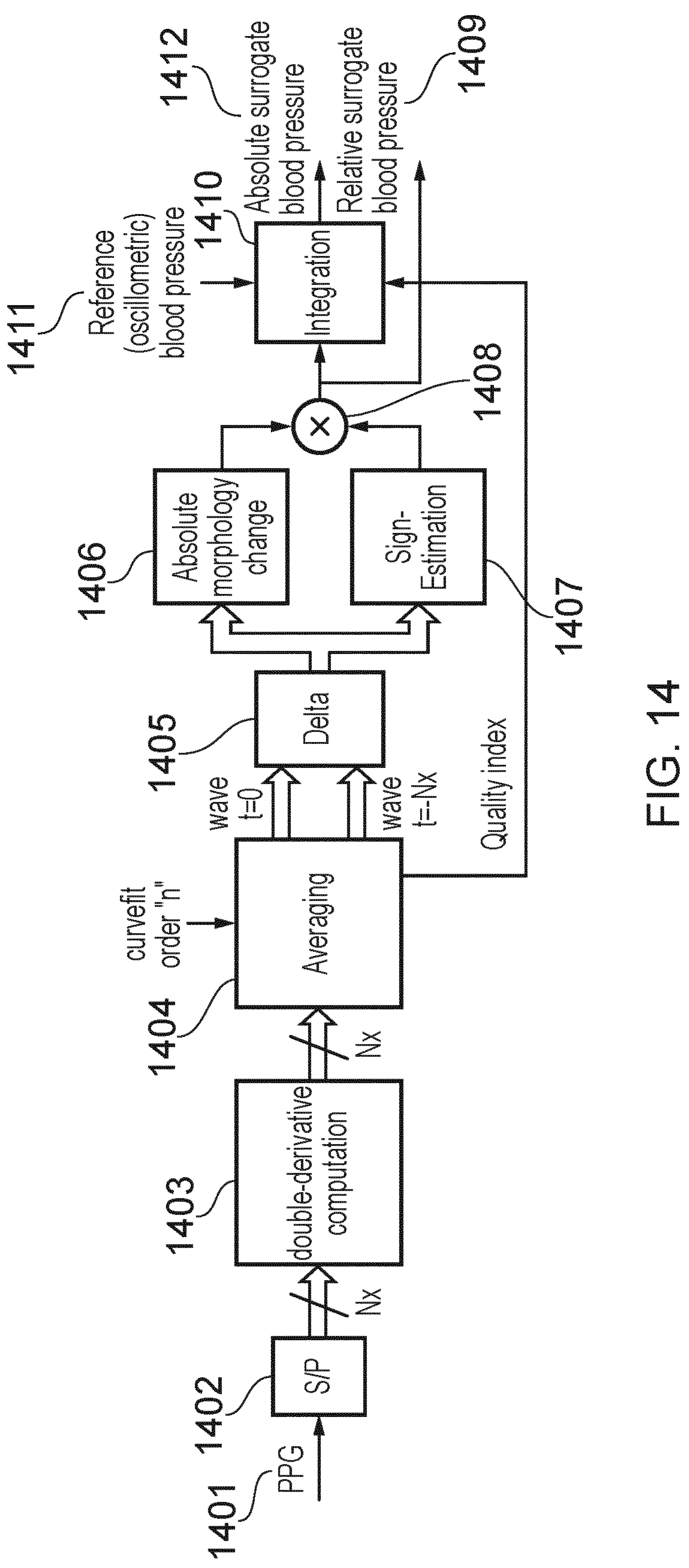
FIG. 14 is a functional block diagram illustrating various operations in analysing a pulse wave signal according to various embodiments.

FIG. 14 is a functional block diagram illustrating various operations in analysing a PWS according to various exemplary embodiments. The various operations and functions shown in FIG. 14 can be implemented by the processing unit 34 shown in FIG. 3. In this exemplary illustrated embodiment, the PWS is a PPG signal 1401. The PPG signal 1401 is input to a Serial/parallel (S/P) Converter 1402 which splits or divides the PPG signal 1401 into one or more windows of $N_x$ samples. The windows of the PPG signal may overlap or be contiguous. The windowed PPG signal is received by a Derivative Computation block 1403 that determines the second order derivative of the PPG signal with respect to time (2PPG).

The 2PPG is input to an Averaging block 1404. The Averaging block 1404 can implement any of the techniques described herein to determine first and second average cardiac cycle waveforms from the 2PPG. In embodiments where the Averaging block 1404 implements the method described above with reference to FIG. 4, a desired value of n for the polynomial fit ('curvefit') is input to the Averaging block 1404. Alternatively the desired value of n can be predetermined or preset in the Averaging block 1404. The Averaging block 1404 outputs a first average cardiac cycle waveform for a particular time point in the windowed PPG signal, and a second average cardiac cycle waveform for another particular time point in the windowed PPG signal. Furthermore, the averaging block 1404 outputs a measure of the quality (e.g. 'quality index') that is input to the integration block 1410 that computes the absolute blood pressure. In FIG. 14 the Averaging block 1404 is shown as outputting an average cardiac cycle waveform for t=0 and $t=-N_x$ (e.g. 1 minute prior to t=0).

The average cardiac cycle waveforms are input to Delta block 1405 which determines the difference signal (representing the change in morphology) from the first and second average cardiac cycle waveforms. The Delta block 1405 can operate as described above with reference to step 113 of FIG. 11. The delta or difference signal is output to an Absolute Morphology Change block 1406 and a Sign Estimation block 1407.

The Absolute Morphology Change block 1406 determines the absolute value of the change in morphology from the difference signal. The Absolute Morphology Change block 1406 can operate as described above with reference to step 115 of FIG. 11.

The Sign Estimation block 1407 determines the direction of the change in morphology from the difference signal. This direction of change corresponds to the direction of blood pressure change. The Sign Estimation block 1407 can operate as described above with reference to step 117 of FIG. 11.

The outputs of the Absolute Morphology Change block 1406 and the Sign Estimation block 1407 are provided to a Multiplication block 1408 which multiplies the absolute value of the change in morphology and the direction of the change to determine the surrogate relative blood pressure change measurement 1409. The surrogate relative blood pressure change measurement 1409 can be output to a user, e.g. a care provider, physician, or the subject themselves.

In embodiments where an absolute blood pressure is to be determined, the surrogate relative blood pressure change measurement 1409 is input to an Integration block 1410, which integrates the relative blood pressure change measurement 1409 with respect to time. The measure of quality that was computed in the averaging block 1404 is used as a weighting factor for the integration to suppress the integration of relative blood pressure change measurements when they are of poor quality. One or more reference blood pressure measurements 1411, for example obtained using oscillometric measurement techniques, are used to calibrate the integration of the relative blood pressure change measurement 1409. The output of the Integration block 1410 is a surrogate absolute blood pressure measurement 1412. The surrogate absolute blood pressure change measurement 1412 can be output to a user, e.g. a care provider, physician, or the subject themselves.

Figure 15:
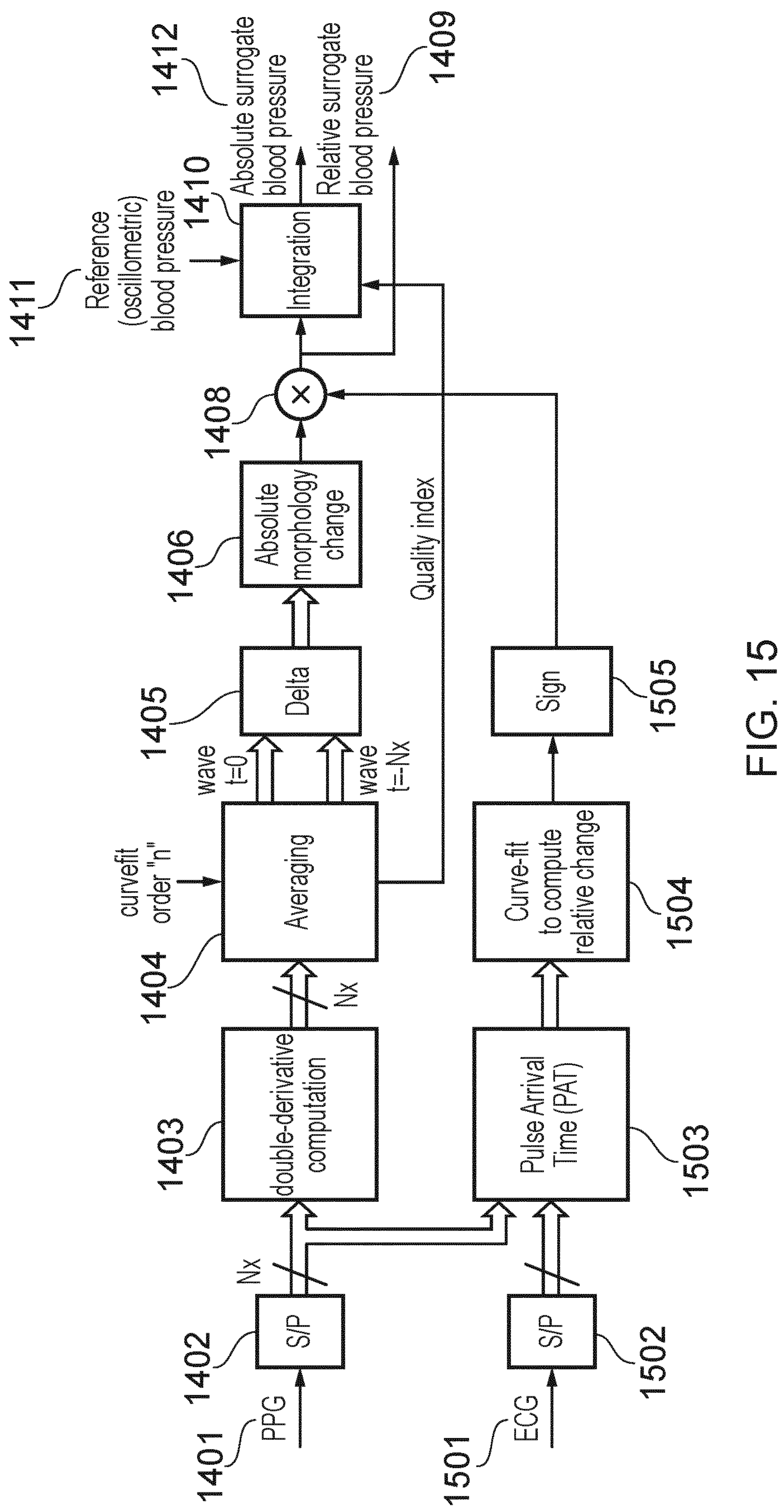
FIG. 15 is a functional block diagram illustrating various operations in analysing a pulse wave signal according to various alternative embodiments.

FIG. 15 is a functional block diagram illustrating various operations in analysing a PWS according to various alternative exemplary embodiments. In these embodiments, rather than estimate the direction of the change in morphology from the difference signal, the direction of the morphology change (i.e. the sign estimation) is determined from a PAT signal for the subject instead. The various operations and functions shown in FIG. 15 can be implemented by the processing unit 34 shown in FIG. 3. Operations and functions in FIG. 15 that are also common to the operations and functions shown in the embodiment of FIG. 14 use the same reference numerals. As in FIG. 14, in this exemplary illustrated embodiment, the PWS is a PPG signal 1401.

The PPG signal 1401 is input to a S/P Converter 1402 which splits or divides the PPG signal 1401 into one or more windows of $N_x$ samples. The windows of the PPG signal may overlap or be contiguous. The windowed PPG signal is received by a Derivative Computation block 1403 that determines the second order derivative of the PPG signal with respect to time (2PPG).

The 2PPG is input to an Averaging block 1404. The Averaging block 1404 can implement any of the techniques described herein to determine first and second average cardiac cycle waveforms from the 2PPG. In embodiments where the Averaging block 1404 implements the method described above with reference to FIG. 4, a desired value of n for the polynomial fit ('curvefit') is input to the Averaging block 1404. Alternatively the desired value of n can be predetermined or preset in the Averaging block 1404. The Averaging block 1404 outputs a first average cardiac cycle waveform for a particular time point in the windowed PPG signal, and a second average cardiac cycle waveform for another particular time point in the windowed PPG signal. In FIG. 14 the Averaging block 1404 is shown as outputting an average cardiac cycle waveform for t=0 and t=$-N_x$ (e.g. 1 minute prior to t=0). Furthermore, the averaging block 1404 outputs a measure of the quality (e.g. 'quality index') that is input to the integration block 1410 that computes the absolute blood pressure.

The average cardiac cycle waveforms are input to Delta block 1405 which determines the difference signal (representing the change in morphology) from the first and second average cardiac cycle waveforms. The Delta block 1405 can operate as described above with reference to step 113 of FIG. 11. The delta or difference signal is output to an Absolute Morphology Change block 1406.

The Absolute Morphology Change block 1406 determines the absolute value of the change in morphology from the difference signal. The Absolute Morphology Change block 1406 can operate as described above with reference to step 115 of FIG. 11. The output of the Absolute Morphology Change block 1406 is provided to a Multiplication block 1408.

As noted above, the direction of the morphology change (i.e. the sign estimation) is determined from a PAT signal for the subject. Thus, an ECG signal 1501 is input to a S/P Converter 1502 which splits or divides the ECG signal 1501 into one or more windows of $N_x$ samples, the same as for the PPG signal 1401. That is, the same windows are applied to the PPG signal 1401 and the ECG signal 1501 so that the direction of morphology change is computed for the same time period.

The windowed ECG signal is input to a PAT block 1503, along with the windowed PPG signal from the S/P Converter 1402, and a PAT signal is determined. The PAT signal indicates the PAT for the subject over time and comprises the PAT for each cardiac cycle in the window. The PAT for a particular cardiac cycle is given by the time from an R-peak in the ECG signal 1501 to that pulse arriving in the PPG signal 1401.

The output of the PAT block 1503 is input to a Curve-fit block 1504 that computes a relative PAT change as given by the equation:

$$\Delta\hat{R}_{PAT}(\kappa) = \frac{\Delta PAT(\kappa)}{PAT(\kappa)}, \tag{26}$$

where the relative PAT change is computed in a similar way as in Equation (12) using all the PAT values in the considered window, using a curve-fit procedure on the PAT values for computing $\Delta PAT(\kappa)$ and using a regular average for computing $PAT(\kappa)$.

After computing the relative PAT change, this information can be combined with the relative morphology change metric described above. By means of experiments it is seen that the relative morphology change metric outperforms the PAT change metric when it comes to the detection of events where the blood pressure changes significantly. However, the direction of change (given by the sign estimation) is better for the PAT than compared to the morphology-based method. Hence, beneficially, the absolute change can be computed by exploiting the PPG morphology change whereas the direction of change can be computed by exploiting PAT measurements and looking at the sign of $\Delta\hat{R}_{PAT}(\kappa)$.

The sign block 1505 determines the sign (either −1 or 1) based on the value of $\Delta\hat{R}_{PAT}(\kappa)$ as computed in the PAT block. When $\Delta\hat{R}_{PAT}(\kappa)<0$, we have a positive sign (i.e. blood pressure is increasing), whereas when $\Delta\hat{R}_{PAT}(\kappa)>=0$, we have a negative sign (i.e. blood pressure is decreasing).

The Multiplication block 1408 multiplies the absolute value of the change in morphology and the direction of the change from Sign block 1505 to determine the surrogate relative blood pressure change measurement 1409. The surrogate relative blood pressure change measurement 1409 can be output to a user, e.g. a care provider, physician, or the subject themselves.

In embodiments where an absolute blood pressure is to be determined, the surrogate relative blood pressure change measurement 1409 is input to an Integration block 1410, which integrates the relative blood pressure change measurement 1409 with respect to time. The measure of quality that was computed in the averaging block 1404 is used as a weighting factor for the integration to suppress the integration of relative blood pressure change measurements when they are of poor quality. One or more reference blood pressure measurements 1411, for example obtained using oscillometric measurement techniques, are used to calibrate the integration of the relative blood pressure change measurement 1409. The output of the Integration block 1410 is a surrogate absolute blood pressure measurement 1412. The surrogate absolute blood pressure change measurement 1412 can be output to a user, e.g. a care provider, physician, or the subject themselves.

It will be appreciated that the embodiment shown in FIG. 15 requires an extra signal/sensor to compute the pulse arrival time (PAT), and the ECG signal needs to be captured synchronously, e.g. within roughly millisecond accuracy, with the PPG signal to enable accurate PAT measurements. As this requirement is not always easy to meet in practice, particularly where the apparatus 30 is to be used in a home environment, and the additional sensor can reduce the ease of use of the apparatus 30, the embodiments shown in FIG. 14 are more preferable than the embodiment in FIG. 15.

Therefore there is provided techniques for the improved estimation of blood pressure changes or blood pressure of a subject.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method for analysing a pulse wave signal (PWS) obtained from a subject to determine an indication of a blood pressure or a change in blood pressure of the subject, wherein the PWS comprises pulse wave measurements for a plurality of cardiac cycles of the subject during a first time period, the method comprising:

(i) analysing the PWS to determine a first average cardiac cycle waveform for a first time point in the first time period and a second average cardiac cycle waveform for a second time point in the first time period;

(ii) determining a difference signal representing a change in morphology from the first average cardiac cycle waveform to the second average cardiac cycle waveform;

(iii) determining an absolute value of the change in morphology from the difference signal;

(iv) determining a direction of the change in morphology; and (v) determining a relative blood pressure change by combining the absolute value and the direction of the change in morphology.

2. The method as claimed in claim 1, wherein the method further comprises:

(vi) integrating the relative blood pressure change with respect to time to determine an estimate of blood pressure of the subject.

3. The method as claimed in claim 2, wherein step (vi) comprises determining the estimate of blood pressure using the absolute value, the direction of the change in morphology, and a first measure of quality of the relative blood pressure change.

4. The method as claimed in claim 3, wherein step (vi) further comprises determining the first measure of quality of the relative blood pressure change by computing a goodness of fit of the first and second average cardiac waveform to the plurality of cardiac cycles in the PWS.

5. The method as claimed in claim 1, wherein the difference signal comprises respective difference samples for a plurality of lag time values measured with respect to a respective reference point for the first average cardiac cycle waveform and the second average cardiac cycle waveform, wherein a difference sample for a particular lag time value is the difference between the first average cardiac cycle waveform at the particular lag time value and the second average cardiac cycle waveform at the particular lag time value.

6. The method as claimed in claim 5, wherein the reference point is an onset of a pulse wave of the subject, and wherein the plurality of lag time values are lag time values from 0 milliseconds to 300 milliseconds after the reference point.

7. The method as claimed in claim 5, wherein step (iv) comprises:

determining a sum of the difference samples for a subset of the plurality of lag time values;

and determining the direction of the change in morphology as the sign of the sum of the difference samples.

8. The method as claimed in claim 7, wherein the reference point is an onset of a pulse wave of the subject, and wherein the subset of the plurality of lag time values are lag time values after the reference point.

9. A computer program product comprising a non-transitory computer readable medium having computer readable code embodied therein, the computer readable code being configured such that, on execution by a suitable computer or processor, the computer or processor is caused to perform the method of claim 1.

10. An apparatus for analysing a pulse wave signal (PWS) obtained from a subject to determine an indication of a blood pressure or a change in blood pressure of the subject, wherein the PWS comprises pulse wave measurements for a plurality of cardiac cycles of the subject during a first time period, the apparatus comprising an input interface configured to receive the PWS, the apparatus configured to:

(i) analyse the PWS to determine a first average cardiac cycle waveform for a first time point in the first time period and a second average cardiac cycle waveform for a second time point in the first time period;

(ii) determine a difference signal representing a change in morphology from the first average cardiac cycle waveform to the second average cardiac cycle waveform;

(iii) determine an absolute value of the change in morphology from the difference signal;

(iv) determine a direction of the change in morphology; and (v) determine a relative blood pressure change by combining the absolute value and the direction of the change in morphology.

11. The apparatus as claimed in claim 10, wherein the apparatus is further configured to:

(vi) integrate the relative blood pressure change with respect to time to determine an estimate of blood pressure of the subject.

12. The apparatus as claimed in claim 11, wherein operation (vi) comprises determining the estimate of blood pressure using the absolute value, the direction of the change in morphology, and a first measure of quality of the relative blood pressure change.

13. The apparatus as claimed in claim 12, wherein operation (vi) further comprises determining the first measure of quality of the relative blood pressure change by computing a goodness of fit of the first and second average cardiac waveform to the plurality of cardiac cycles in the PWS.

14. The apparatus as claimed in claim 10, wherein the difference signal comprises respective difference samples for a plurality of lag time values measured with respect to a respective reference point for the first average cardiac cycle waveform and the second average cardiac cycle waveform, wherein a difference sample for a particular lag time value is the difference between the first average cardiac cycle waveform at the particular lag time value and the second average cardiac cycle waveform at the particular lag time value.

15. The apparatus as claimed in claim 14, wherein the reference point is an onset of a pulse wave of the subject, and wherein the plurality of lag time values are lag time values from 0 milliseconds to 300 milliseconds after the reference point.

* * * * *